(12) United States Patent
Lee et al.

(10) Patent No.: US 11,508,472 B2
(45) Date of Patent: Nov. 22, 2022

(54) HEALTH TRACKING SYSTEM WITH VERIFICATION OF NUTRITION INFORMATION

(71) Applicant: MYFITNESSPAL, INC., San Francisco, CA (US)

(72) Inventors: Chul Lee, San Francisco, CA (US); Hesamoddin Salehian, San Francisco, CA (US)

(73) Assignee: MyFitnessPal, Inc., San Francisco, CA (US)

( * ) Notice: Subject to any disclaimer, the term of this patent is extended or adjusted under 35 U.S.C. 154(b) by 483 days.

(21) Appl. No.: 15/093,191

(22) Filed: Apr. 7, 2016

(65) Prior Publication Data

US 2017/0286062 A1    Oct. 5, 2017

Related U.S. Application Data

(63) Continuation of application No. 15/087,646, filed on Mar. 31, 2016.

(51) Int. Cl.
| | |
|---|---|
| *G16H 20/60* | (2018.01) |
| *G06F 7/36* | (2006.01) |
| *G16H 50/30* | (2018.01) |
| *G16H 10/60* | (2018.01) |

(52) U.S. Cl.
CPC .......... *G16H 20/60* (2018.01); *G06F 7/36* (2013.01); *G16H 10/60* (2018.01); *G16H 50/30* (2018.01)

(58) Field of Classification Search
CPC ........ G06F 7/36; G06F 19/3475; G16H 50/30

USPC ......................................................... 707/696
See application file for complete search history.

(56) References Cited

U.S. PATENT DOCUMENTS

| | | | |
|---|---|---|---|
| 8,626,796 B2 * | 1/2014 | McBride | G06F 19/3475 707/796 |
| 8,719,244 B1 * | 5/2014 | Pasca | G06F 17/30864 707/706 |
| 9,619,582 B1 | 4/2017 | Djabarov et al. | |

(Continued)

OTHER PUBLICATIONS

Koga, Hisashi, Tetsuo Ishibashi, and Toshinori Watanabe. "Fast agglomerative hierarchical clustering algorithm using Locality-Sensitive Hashing." Knowledge and Information Systems 12.1 (2007): 25-53. (Year: 2007).*

(Continued)

*Primary Examiner* — Mohsen Almani
(74) *Attorney, Agent, or Firm* — Maginot, Moore & Beck, LLP

(57) ABSTRACT

A method for decreasing a number of individual entries in a database of user-created records which describe a single item by: receiving a plurality of user-created records, each of said records comprising at least a descriptive string; placing individual ones of the plurality of user-created records having a sufficiently similar descriptive string into one of a plurality of first groups; hashing the descriptive string of each of the plurality of first groups in order to place two or more groups into a single bin; performing a pair-wise comparison of the descriptive strings of the two or more groups in each bin; and when the comparison of the descriptive strings of the two or more groups in a bin results in a distance below a first threshold, merging the two or more groups into a combined group.

16 Claims, 12 Drawing Sheets

(56) References Cited

U.S. PATENT DOCUMENTS

| | | | |
|---|---|---|---|
| 2005/0113650 A1* | 5/2005 | Pacione | A61B 5/411 |
| | | | 600/300 |
| 2009/0148818 A1* | 6/2009 | Li | G09B 19/0092 |
| | | | 434/127 |
| 2009/0300007 A1* | 12/2009 | Hiraoka | G06F 17/30011 |
| 2016/0071431 A1 | 3/2016 | Jain | |
| 2016/0379520 A1* | 12/2016 | Borel | G09B 19/0092 |
| | | | 434/127 |
| 2017/0091343 A1 | 3/2017 | Shorina et al. | |
| 2020/0082169 A1* | 3/2020 | Lu | G16H 50/30 |

OTHER PUBLICATIONS

Kontorovich, Aryeh, and Ari Trachtenberg. "String reconciliation with unknown edit distance." Information Theory Proceedings (ISIT), 2012 IEEE International Symposium on. IEEE, 2012. (Year: 2012).*

Lambert, Bruce L., et al. "Similarity as a risk factor in drug-name confusion errors: the look-alike (orthographic) and sound-alike (phonetic) model." Medical care (1999): 1214-1225. (Year: 1999).*

Hochuli, Alexandra, Data Cleansing for Food Composition Data, Global Information Systems Group, Institute of Information Systems, Department of Computer Science, Apr. 7, 2014.

Bilenko, Mikhail et al., Adaptive Product Normalization: Using Online Learning for Record Linkage in Comparison Shopping, Proceedings of the 5th International Conference on Data Mining, Nov. 2005, pp. 58-65, Houston, TX.

Kennedy, Eileen T. et al., The healthy eating index: design and applications, Journal of the American Dietetic Association 95.10, 1995, pp. 1103-1108.

* cited by examiner

HEALTH TRACKING SYSTEM WITH VERIFICATION OF NUTRITION INFORMATION

CROSS-REFERENCE TO RELATED APPLICATIONS

This patent document is a continuation of and claims priority from U.S. patent application Ser. No. 15/087,646, filed Mar. 31, 2016, the contents of which are incorporated herein by reference in their entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD

This disclosure relates to the field health tracking. More particularly, the present disclosure relates to methods, systems, computer programs, and devices configured to enable collection and display of food consumption information for a user.

BACKGROUND

Health tracking systems are increasingly utilized by individuals interested in tracking metrics related to their personal health and fitness. These health systems typically include a user interface provided on a health tracking device such as a smartphone, laptop computer, or desktop computer. The user interface provides the user with any of various health, fitness and activity related data such as food/beverage and nutritional consumption, calorie expenditure, heart rate, distance travelled, steps taken, etc.

Health tracking systems often collect certain health, fitness, and/or activity-related data automatically. However, other data must be logged manually such as by the user. For example, food consumption data must typically be logged by the user by e.g. searching food items in a database and selecting those food items as food consumed by the user. The database of food items typically includes a significant number of entries that were created by other individual users without any review, verification, and/or validation of the information contained therein. Accordingly, the nutrition data associated with food items that represent the same food in the database is often incomplete and/or inconsistent between food items.

Because of the incomplete and/or inconsistent nutrition data between food items, logging food consumption data in the health tracking system can be challenging for users. If the user searches for a particular food item to log, the user is often presented with multiple choices for the same food item, with each of the multiple food items presenting different nutrition data. For example, if the user wishes to log consumption of an apple into the health tracking system, he or she may search for "apple" via the user interface. This search may result in several possible food item choices presented to the user, but each of the food item choices may present different nutrition data. One "apple" food item presented to the user may indicate that an apple has one hundred calories, while another "apple" food item may indicate that an apple has only eighty calories. Determining which of these choices is the proper food item choice for the user is often difficult. Similar difficulties are encountered by users with respect to entry relating to the consumption of beverage and other consumable items.

In view of the foregoing, it would be advantageous to provide a health tracking system and related method that allows the user to more quickly and easily select food and beverage items from the database of a health tracking system. It would also be advantageous if such a system and method provided the user with more accurate nutrition data for each item logged by the user.

SUMMARY

In accordance with one exemplary embodiment of the disclosure, there is provided a method of operating a health tracking system comprising receiving a plurality of data relating to a respective plurality of consumables from a plurality of health tracking devices. The method further comprises storing the plurality of data as a plurality of data records in a database, each of the plurality of data records comprising at least a description string. Additionally, the method comprises grouping the plurality of data records into a plurality of groups based at least on the description string of each, each of the plurality of groups comprising at least one reliable data record. The method also comprises performing one or more comparison steps relating to the descriptive strings of each of the plurality of groups in order to identify at least two of the plurality of groups which are to be merged into a combined group. Additionally, the method comprises selecting one of the reliable data records of the merged at least two groups as a reliable data record for the combined group.

Pursuant to another exemplary embodiment of the disclosure, there is provided a non-transient computer readable medium comprising a plurality instructions which are configured to, when executed, decrease a number of individual entries in a database of user created data records relating to a single consumable item. Execution of the plurality of instructions cause a computerized apparatus to receive the plurality of user created data records from a plurality of user devices and store the plurality of user created data records in the database, each of the plurality of user created data records including at least a description string. Execution of the plurality of instructions further causes the computerized apparatus to place each of the plurality of user created data records into one of a plurality of groups based at least in part on the description string associated thereto such that individual ones of the plurality of user created data records having description strings which are identical are placed in a same one of said plurality of groups. Additionally, execution of the plurality of instructions further causes the computerized apparatus to merge at least two of the plurality of groups into a combined group via application of a comparison operation to the description strings thereof, and select one of the data record in the combined group as a reliable data record for the combined group . . . .

In accordance with yet another exemplary embodiment of the disclosure, there is provided a method for decreasing a number of individual entries in a database of user-created records which describe a single item. The method comprises receiving a plurality of user-created records, each of said records comprising at least a descriptive string, and placing individual ones of the plurality of user-created records having a sufficiently similar descriptive string into one of a plurality of first groups. The method further comprises hashing the descriptive string of each of the plurality of first groups in order to place two or more groups into a single bin, and performing a pair-wise comparison of the descriptive strings of the two or more groups in each bin. When the comparison of the descriptive strings of the two or more groups in a bin results in a distance below a first threshold, the two or more groups are merged into a combined group . . . .

The above described features and advantages, as well as others, will become more readily apparent to those of ordinary skill in the art by reference to the following detailed description and accompanying drawings. While it would be desirable to provide a health tracking system that provides one or more of these or other advantageous features, the teachings disclosed herein extend to those embodiments which fall within the scope of the appended claims, regardless of whether they accomplish one or more of the above-mentioned advantages.

BRIEF DESCRIPTION OF THE DRAWINGS

FIG. 4 is a plan view of a graphical user interface of the display device of

FIG. 2;

All Figures © Under Armour, Inc. 2016. All rights reserved.

DESCRIPTION

Disclosed embodiments include systems, apparatus, methods and storage medium associated with health tracking in general, and in particular enabling collection and display of food and/or beverage information related to a user.

In the following detailed description, reference is made to the accompanying drawings which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

Figure 1:
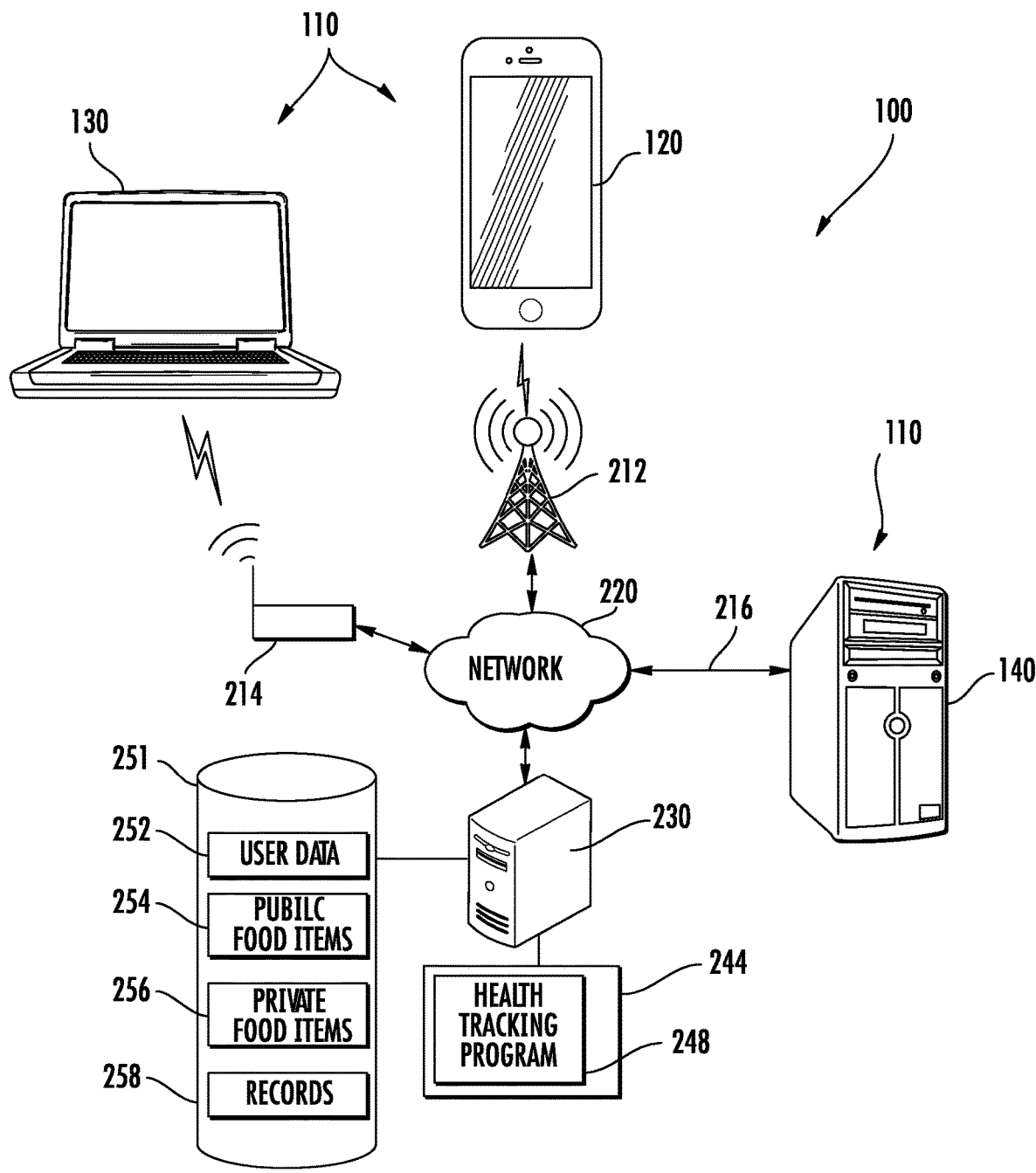
FIG. 1 is a diagrammatic view showing an exemplary embodiment of a health tracking system including a plurality of health tracking devices connected to a host server over a network.

With reference to FIG. 1, an exemplary embodiment of a health tracking system 100 is shown. In the illustrated embodiment, the health tracking system 100 includes a plurality of third party health tracking devices 110 in communication with a server 230 or other host computing device over a network 220 such as, e.g., the Internet. The server 230 is configured to receive entries of nutrient component and/or caloric values of consumables from the health tracking devices 110 and other regulated entities, store the entries as consumable items in a database 251 for later reference, and identify certain items in the database 251 as so called "verified items". The server 230 makes all of the consumable items in the database 251 available for the health tracking devices 110. Specifically, the health tracking devices 110 are configured to access and search the database 251 of consumable items, display the items, including the verified items, and enable the user to select individual ones of the displayed items for purposes of nutrition logging. As used herein, the term "food" is used interchangeably with the word "consumable" to generally refer to one or more foods, beverages, and other consumables such as vitamins, supplements, medications, etc.

Health Tracking Devices

The health tracking device 110 may be provided in any of various forms. Examples of a health tracking devices 110 configured for use with the health tracking system 100 include a smartphone 120, a laptop computer 130, and a desktop computer 140, as shown in FIG. 1. Accordingly, it will be recognized that the health tracking devices 110 may comprise portable electronic devices such as the smartphone 120 or the laptop computer 130, or stationary electronic devices such as the desktop computer 140. Other examples of health tracking devices include, handheld or tablet computers, smart watches, portable media players, or any of various other health tracking devices configured to receive entry of consumed items (not shown). In another embodiment, also illustrated in FIG. 1, data entered at one device 110 may be provided to other ones of the user's devices 110. For example, data entered at the smart phone device 120 may be provided to the desktop computer 140 and/or the laptop computer 130 for storage thereat. As shown in FIG. 1, the health tracking devices 110 are generally configured to utilize any of various wired or wireless communications components, infrastructures and systems, such as cell towers 212 of a mobile telephony network, wireless routers 214, Bluetooth®, near field communication (NFC), or physical cables 216.

Figure 2:
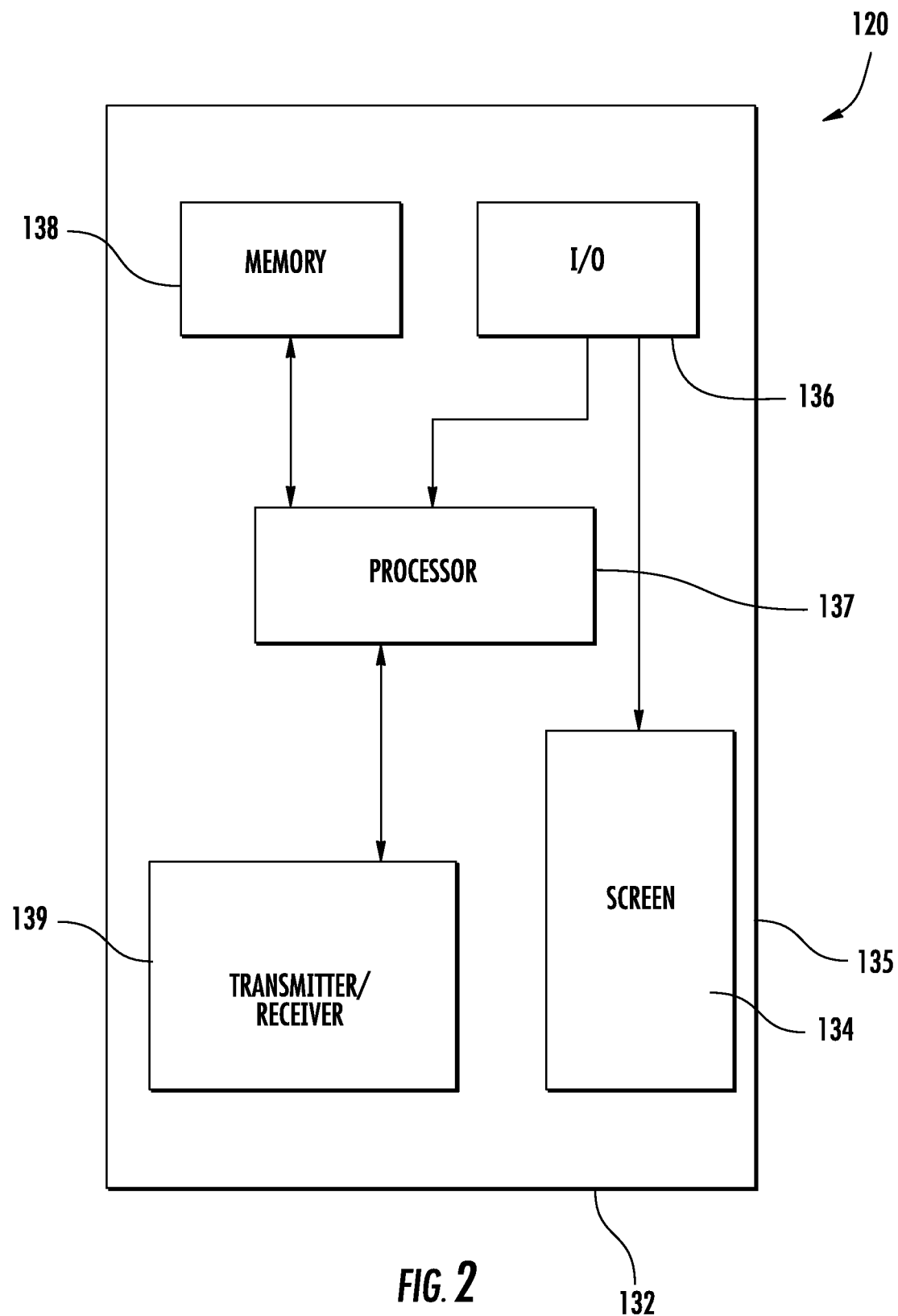
FIG. 2 is a block diagram of exemplary electronic components of one of the health tracking devices of FIG. 1.

With reference now to FIG. 2, an exemplary health tracking device 110 in the form of a smartphone 120 is shown. The smartphone 120 includes a display screen 134, an input/output interface 136, a processor 137, a memory 138, and one or more transceivers 139. The smartphone 120 also includes a protective outer shell or housing 132 designed to retain and protect the electronic components positioned within the housing 132. The smartphone 120 also includes a battery (not shown) or other power source configured to power the display screen 134, processor 137, transceivers 139 and various other the electronic components within the smartphone 120. As will be recognized by those of ordinary skill in the art, the components of the health tracking device 110 may vary from device to device. Such alternative health tracking devices 110 may include much (but not necessarily all) of the same functionality and components as the smartphone 120 shown in FIG. 2, as well as additional functionality or components necessary for proper functioning thereof.

The I/O interface 136 of the smartphone 120 includes software and/or hardware configured to facilitate communications with other network components or the user him/herself. The hardware of the I/O interface may include e.g., the display screen 134 which is configured to visually display graphics, text and other data to the user. The display screen 134 of the smartphone 120 may be an LED screen or any of various other screens appropriate for the health tracking device. In at least one embodiment, the display screen 134 is an LED-backlit touchscreen that allows the user to make selections, type, or otherwise provide input directly on the screen using his or her finger or a stylus device. In addition to the display screen 134, the I/O interface 136 may include additional hardware such as a microphone and/or speakers to facilitate audio communications with the user and/or verbal entry of commands to the smartphone 120.

The processor 137 of the smartphone 120 may be any of various processors as will be recognized by those of ordinary skill in the art. The processor 137 is in data communication with the I/O interface 136, the memory 138, and transceivers 139, and is configured to deliver data to and receive data from each of these components. It will be recognized by those of ordinary skill in the art that the term "processor" as used herein includes any hardware system, hardware mechanism or hardware component that processes data, signals or other information. A processor can include a system with a central processing unit, multiple processing units, dedicated circuitry for achieving functionality, or other systems.

The memory 138 is configured to store information, including data and instructions for execution by the processor 137. The data may include any of various types of data that may be useful to the operation of the health tracking device and any associated applications. As explained in further detail below, the data stored in the memory 138 may include a plurality of records relating to the nutritional and/or caloric content of consumables or food items provided from the database 251 of the host server 230. The instructions which are also stored in the memory 138 may include instructions for display of an interactive graphical user interface provided by a health tracking application on the smartphone 120. The health tracking application may be downloaded from the host server 230 for execution on the user's health tracking device 110; or alternatively, may be preloaded on the device at time of manufacture. Operation of such a health tracking app and exemplary uses of the data is described in further detail below.

The memory 138 that retains the data and instructions may be of any type of device capable of storing information accessible by the processor, such as a memory card, ROM, RAM, write-capable memories, read-only memories, hard drives, discs, flash memory, or any of various other computer-readable medium serving as data storage devices as will be recognized by those of ordinary skill in the art. Portions of the system and methods described herein may be implemented in suitable software code that may reside within the memory as software or firmware. Such software code may be present in the health tracking device 110 at the time of manufacture or may be downloaded thereto via well-known mechanisms. A computer program product implementing an embodiment disclosed herein may therefore comprise one or more computer-readable storage media comprising computer instructions translatable or executable by a processor and configured to enable the processor to provide an embodiment of a system or perform an embodiment of a method disclosed herein. Computer instructions may be provided by lines of code in any of various languages as will be recognized by those of ordinary skill in the art. Moreover, a "non-transient computer-readable medium" may be any type of data storage medium that can store computer instructions, including, but not limited to the memory devices discussed above.

The transceivers 139 may be any of various transceivers configured for wireless or wired communication with other electronic devices, including the ability to send and receive communication signals. The transceivers 139 may include one or more of any of various different types of transceivers configured to communicate with different networks and systems. Such transceivers are well known and will be recognized by those of ordinary skill in the art. The transceivers typically perform wireless communications. However, in at least one embodiment, the transmitters may be used in association with data ports which employ a physical (i.e., wired) connection to another device prior to transmission of the data.

In at least one embodiment, the transceivers 139 are configured to enable the smartphone 120 to perform wireless communications with a wireless telephony network, as will be recognized by those of ordinary skill in the art. The wireless telephony network may comprise any of several known or future network types. For example, the wireless telephony network may comprise commonly used cellular phone networks using CDMA, GSM or FDMA communication schemes, as well as various other current or future wireless telecommunications arrangements.

In the embodiment of FIG. 2 wherein the health tracking device 110 is a smartphone 120, the transceivers 139 may further include GPS receivers configured to receive GPS signals from GPS satellites 202. Accordingly, the smartphone 120 or other health tracking device may be a geoposition enabled device configured to determine its location based on received signals utilized by the health tracking system 100. While the smartphone 120 is described herein as being a GPS-enabled device, it will be appreciated that in other embodiments, other geo-position devices may be provided utilizing signals and technologies other than GPS.

In addition to transceivers 139 configured to communicate with the cellular towers 212 of a wireless telephony network, and receive signals from GPS satellites 202, the transceivers 139 may also be configured to communicate with any of various other electronics devices and networks using any of various communication schemes. For example, the transceivers 139 may also be configured to allow the smartphone 120 to communicate with any of various local area networks using WiFi, Bluetooth® or any of various other communications schemes.

Host Data Processing System

Figure 3:
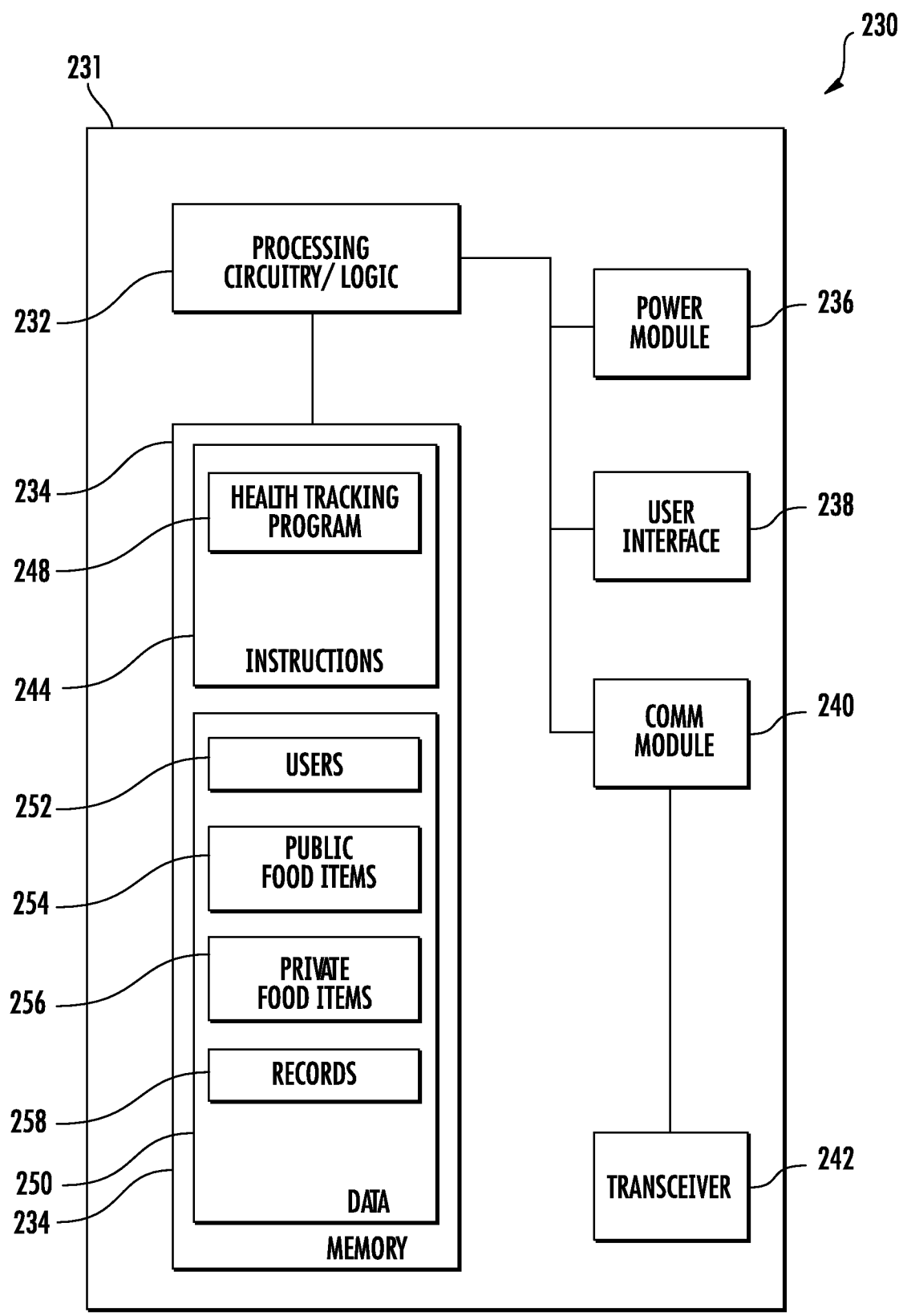
FIG. 3 is a block diagram of exemplary electronic components of the host server of FIG. 1.

With reference now to FIG. 3, a block diagram of an exemplary embodiment of the host server 230 of FIG. 1 is shown. The host server 230 includes processing circuitry/logic 232, memory 234, a power module 236, a user interface 238, a network communications module 240, and a wireless transceiver 242. The components of the host server 230 are typically provided in a housing, cabinet or the like 231 that is configured in a typical manner for a server or related computing device. It is appreciated that the embodiment of the host server 230 shown in FIG. 3 is only one exemplary embodiment of a server 230 for the health tracking system 100. As such, the exemplary embodiment of the host server 230 described herein with reference to FIG. 3 is merely representative of any of various manners or configurations of host servers or other data processing systems that are operative in the manner set forth herein.

The processing circuitry/logic 232 of the host server 230 is operative, configured, and/or adapted to operate the host server 230 including the features, functionality, characteristics and/or the like as described herein. To this end, the processing circuit 232 is operably connected to all of the elements of the host server 230 described below.

The processing circuitry/logic 232 of the host server is typically controlled by the program instructions 244 contained within the memory 234. The program instructions 244 include a health tracking program 248 as explained in further detail below. The health tracking program 248 at the host server 230 is configured to communicate with and exchange data with the client-side health tracking app running on a processor 137 of the health tracking devices 110. In addition to storing the instructions 244, the memory 234 also stores data 250 for use by the health tracking program 248. As explained in further detail below, the data 250 includes the user database 252 (which includes user profile information), public food items database 254, private food items database 256, and records 258. It is noted that although referenced here and in the figures as "food" databases, the information stored therein may comprise data relating to any type of consumable including e.g., food, beverages, vitamins, supplements, medications, etc.

With continued reference to FIG. 3, the power module 236 of the host server 230 is operative, adapted and/or configured to supply appropriate electricity to the host server 230 (i.e., including the various components of the host server 230). The power module 236 may operate on standard 120 volt AC electricity, but may alternatively operate on other AC voltages or include DC power supplied by a battery or batteries.

The network communication module 240 of the host server 230 allows for communication with any of various devices using various means. In one particular embodiment, the network communications module 240 includes a wide area network port that allows for communications with remote computers over the Internet (e.g., network 220 of FIG. 1). The network communications module 240 may further include a local area network port that enables communication with any of various local computers housed in the same or nearby facility. In at least one embodiment, the local area network port is equipped with a WiFi transceiver 242 or other wireless communications device. Accordingly, it will be appreciated that communications with the host server 230 may occur via wired communications or via the wireless communications. Communications may be accomplished using any of various known communications protocols.

The host server 230 may be accessed locally. To facilitate local access, the host server 230 includes an interactive user interface 238. Via the user interface 238, an operator may access the instructions, including the health tracking program 248, and may collect data from and store data to the memory 234. In at least one embodiment, the user interface 238 may suitably include an LCD type screen or the like, a mouse or other pointing device, a keyboard or other keypad, speakers, and a microphone, as will be recognized by those of ordinary skill in the art. Accordingly, the user interface 238 is configured to provide an administrator or other authorized user or operator with access to the memory 234 and allow the authorized user to amend, manipulate and display information contained within the memory.

As mentioned previously, in addition to the instructions 244, the memory 224 also includes data 250. In the illustrated embodiment, the data 250 comprises a user database 252, a public food items database 254, a private food items database 256, and records database 258.

The user database 252 includes data associated with each user of the health tracking system 100, including e.g., user profiles, and consumption data. Each user profile includes demographic information for the user such as name, age, gender, height, weight, performance level (e.g., beginner, intermediate, professional, etc.), and/or other information for the user. Each user profile is associated with consumption data. The consumption data includes information logged by the user related to his or her personal food, beverage, etc. intake. The consumption data typically includes a number of different food and beverage items (and/or other consumables) consumed by the user over a period of time. The consumption data may also include a consumption date and time associated with each logged item. Accordingly, the health tracking system 100 maintains information concerning consumables consumed by the user over a number of days, weeks, months, and/or years. The health tracking system 100 is configured to process this consumption data and present it to the user in a logical format to assist the user with understanding his or her consumption history, tendencies and overall health. Presentation of the consumption data may include presentation of information related to the user's weight and general nutrition intake for any of various health related goals (e.g., weight loss, weight gain, athletic training, etc.).

The public food items database 254 and the private food items database 256 include a plurality of food item data records. The phrase "food item data records" (and the phrase "item data records") as used herein refers to one or more data records stored in a database that are associated with a particular food, beverage, vitamin, supplement, medication, and/or other consumable that may be consumed by a user. Each food item data record typically includes a name for the particular item provided as a description string, summary information about the item which may include summarized or general overview of nutrition data, and more detailed information about the item which includes more detailed nutrition data in addition to that provided in the summary information. The nutrition data about the item may include one or more of serving size, calories, ingredients, nutritional content, or any other nutrition data about the item. For example, the nutrition data may include information that may be provided on a USDA food labels or state-regulated food labels (e.g., vitamin and mineral content, fat content, cholesterol content, protein content, sugar content, carbohydrate content, fiber content, organic contents, etc.). As another example, nutrition data may include the serving size of the food item (e.g., 12 ounces, 16 ounces, 24 ounces, etc.).

Item data records in the public food items database 254 are provided by authorized organizations and not individuals. For example, the item data records in the public food items database 254 may be provided by verified sources such as United States Department of Agriculture (USDA), United States Food and Drug Administration, and/or other government regulated entities. As another example, item data records in the public food items database 254 may be provided by commercial food providers that are required to publish nutrition data for products and/or menu items offered by the commercial food provider. Examples of such commercial food providers include, e.g., Dannon®, Dole®, Kellogg's®, Starbucks®, and Chipotle®, to name a few. Certain item data records in the public food items database 254 may have generic description strings or may have individualized or brand (i.e., trademarked) description strings. Examples of items having generic description strings include "yogurt," "pineapple," "bran flakes," "mocha," and "beef nachos". Examples of items having individualized or brand description strings include "Dannon yogurt," "Dole pineapple," "Kellogg's raisin bran," "Starbucks tall mocha," and "Chipotle beef nachos."

The nutrition data contained within the item data records stored in the public food items database 254 is, in one embodiment, substantially complete and additionally comprises trusted information. For example, food item information which is used to generate the item data records may be received from the USDA or FDA (or from entities regulated thereby) and may have the benefit of having third party scientific validation of the nutrition data generated, created and/or published by the manufacturer. Item data records in the public food items database 254 are not editable by individual users. Instead, only an operator with special authorization or access privileges may edit records in the public food items database 254.

The item data records in the private food items database 256 are provided by individual users of the system 100. For example, the data records in the private food items database 256 may be crowd sourced from numerous individual users of the health tracking system 100. A user may be interested in entering information relating to a particular consumable item if they cannot find that particular item from a search of the existing data 250, and/or if they are unsatisfied with the available selections relating to that particular food which are currently available. Items in the private food items database 256 may have generic description strings, or alternatively, may have individualized or brand recognized description strings. Examples of items having generic description strings include "oatmeal," "chicken parmesan," "chicken burrito," and "shrimp cocktail". Examples of items having individualized or brand description strings include "Laura's oatmeal," "Mike's chicken parmesan," "Chipotle chicken burrito," and "St. Elmo's shrimp cocktail." The nutrition data within the item data records in the private food items database 256 are, in one embodiment, editable by individual users and/or may be created and edited by users without special authorization or permissions. Therefore, because individuals may enter consumables having brand names, it will be recognized that the nutrition data associated with certain items is dependent on the information available to the individual and the individual's care in entering accurate information. Item data records created or entered by individuals often include description strings and nutrition data that is flawed and/or incomplete in such a manner that the record created therefrom does not accurately represent the consumable it purports to represent. Thus, an accuracy of items in the private food items database 256 is, in one embodiment, not guaranteed because these records are generated entirely from individual user inputs. Accordingly, the item data records in the private food items database 256 may be subjected to a verification process, such as that described in further detail below.

With continued reference to FIG. 3, the records database 258 in one embodiment includes current and/or historical data stored by the host server 230 in association with operation of the host server 230, execution of the health tracking program 248, and/or manipulation of data 250 within the memory 234. For example, the records 258 may include information concerning amendments made to any of various item data records in the public food items database 254 and/or the private food items database 256. The records 258 may also include other information related to the control and operation of the host server 230, including statistical, logging, licensing, and/or historical information.

While the host server 230 has been explained in the foregoing embodiments as housing the health tracking program 248 and the various records and databases in the memory 234, it will be recognized that these components may be retained in other locations in association with the health tracking system 100. For example, in at least one embodiment, the public food items database 254 and/or the private food items database 256 may be retained by one or more third party databases separate from yet in communication with the host server 230. In such embodiments, the health tracking app may utilize any number of application programming interfaces (APIs) to access the data in the third party databases and incorporate such information for use in the health tracking program 248. Accordingly, it will be recognized that the description of the host server 230 of FIG. 3 is but one exemplary embodiment of a data processing system that may be utilized by the health tracking system 100.

Health Tracking App With Verified Item Data Records

Figure 4:
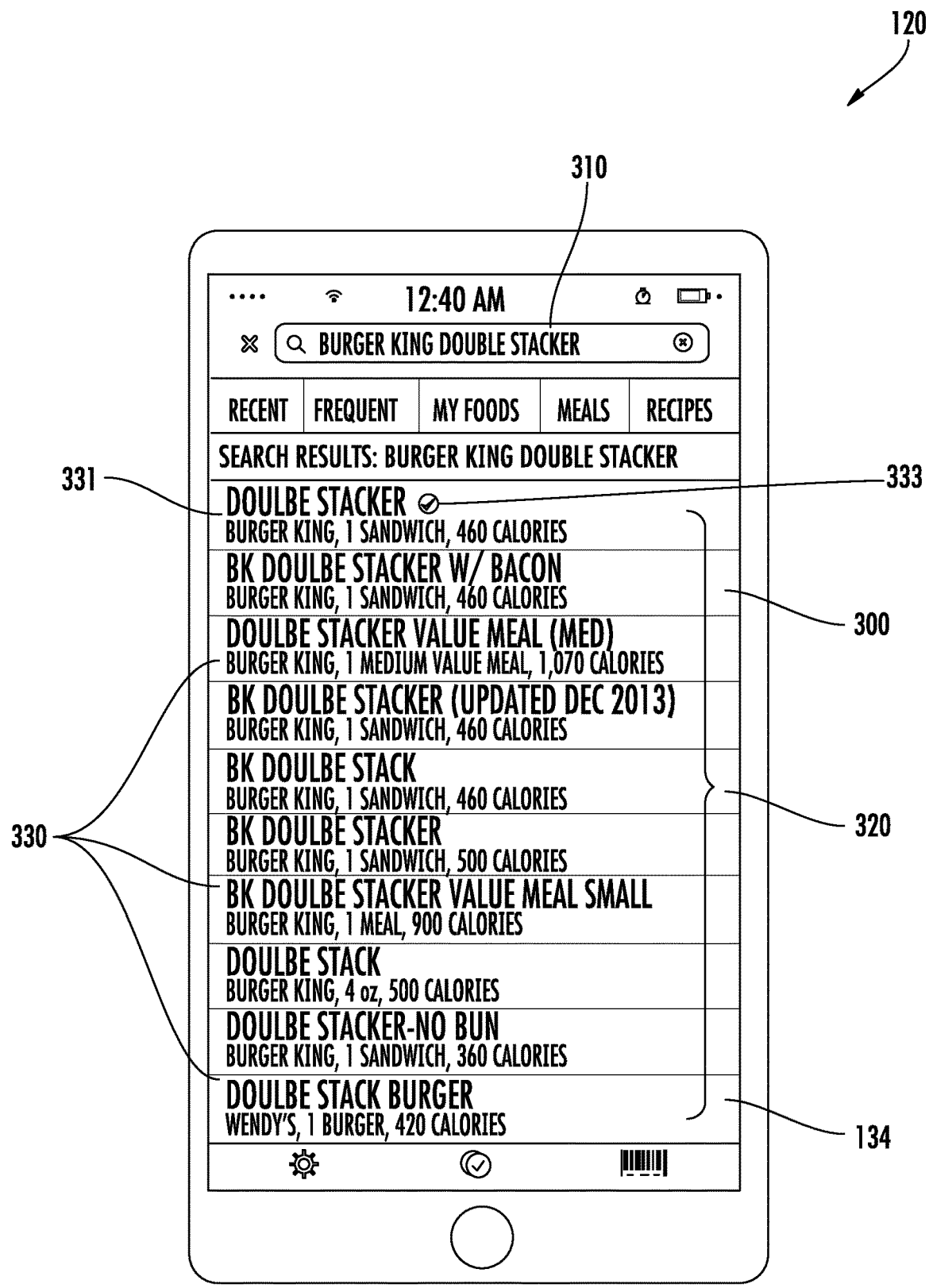

With reference now to FIG. 4, a screen shot of an exemplary graphical user interface 300 of the health tracking app is shown on a user smartphone 120. The graphical user interface 300 includes graphics and data provided by the system server 230 and presented on the user's smartphone 120 or other health tracking device 110 via the network 220. In the embodiment of FIG. 4, the graphical user interface 300 includes a search prompt 310 and a food items listing 320. Text may be entered by the user in the search prompt 310. In response to the user's entry of text, the listing 320 displays a number of item data records 330 retained in the public food items database 254 and/or the private food items database 256 which correspond to the searched consumable.

In the exemplary embodiment of FIG. 4, the user input the search text "Burger king double stacker" in the search prompt 310 and thereby requested a search for consumables and/or item data records matching that search text (e.g., by selecting the magnifying glass icon or selecting the return option after typing the text). In the illustrated example, the search returned a plurality of items 330 determined by the health tracking system as having a description string that sufficiently matches the search text. A set of data records which match the search terms are provided as search results in the list 320. The set of data records includes the ten records 330 displayed on the screen 134 in the list 320 of FIG. 4, however, any number of records may be displayed in accordance with the present disclosure. Additional item data records are also available for viewing if the user scrolls down the items listing 320 in the illustrated embodiment.

Because generation or creation of the item data records in the private food items database 256 is crowd sourced, numerous duplicate entries often exist for a single item type. These duplicate entries comprise different data records representing the same food type, and in one embodiment may be listed or named in various free text formats. For example, the first record 331 in the listing 320 of FIG. 4 is named "Double Stacker", while the second record 332 is named "Bk Double Stacker W/Bacon". Each of the remaining records in the list 320 FIG. 4 includes slightly different variations on the Burger King menu item referred to by the company as a "Double Stacker". Additionally, these multiple entries for the same food result in inconsistent nutrition data. For example, the first data record indicates a total of 490 calories, while the second data record 332 which further includes bacon also indicates a total of "490" calories. A data record further in the list indicates "560" total calories. Such inconsistent and/or incomplete nutrition data may be confusing to the user, therefore the herein disclosed system utilizes the methods discussed elsewhere herein to identify and demarcate at least one item in the listing 320 as a "verified" food item or data record.

With continued reference to FIG. 4, the first item data record 331 displayed on the listing 320 comprises the "verified" food item data record as demonstrated by the icon 333. The remaining item data records displayed in the listing 320 (i.e., all data records other than the first record 331) of the illustrated embodiment comprise non-verified items. A "verified" item is an item data record that has been identified as having trusted nutrition and other data (according to the methods discussed elsewhere herein). An identifier may be applied to the item data record in order to identify the item data record as a verified item data record. The identifier results in an icon, symbol, notation or other marker being displayed in association with the verified item data record. Accordingly, when a user performs a search for a particular food and a list of food data records is returned from the search, the user is able to quickly and easily identify at least one of the returned food data records which includes trusted nutrition data for the particular food.

In FIG. 4, the verified or reliable data record is the first record 331 displayed in the listing 320. In this exemplary embodiment, the verified item data record is identified by an icon 333 next to the item. While a shield with a check mark is used as the icon that identifies the verified item in the embodiment of FIG. 4, it will be recognized different icons, text, symbols, notations, coloration, or other markers may be used to identify a verified or trustworthy item in the list. In at least one embodiment, a "verified" item may comprise an item that is noted as being recommended by the health tracking system for selection by the user within a group of items. Moreover, the placement of "verified" items may be separated spatially from other non-verified items. In another embodiment, the "verified" items may remain at a fixed location on the screen (e.g., the top) despite the user scrolling further into the list.

As noted above, the use of verified or reliable item data records allow the user to quickly identify those items in a given listing that the system has identified as comprising trusted nutrition data. Accordingly, the user may choose to quickly select the verified item data record when presented with a list of item data records without the need to look through the numerous other item data records in the listing. This advantageously saves the user time when logging personal consumption information into the system.

While certain embodiments may provide only a single verified item data record associated with each listing (such as that shown in FIG. 4), it will be recognized that in other embodiments more than one verified item data records may be associated with a particular search result listing. For example, two, three, four or even more verified or trustworthy records may be identified for each listing. In at least one embodiment, each listing may include one verified item data record from the public food items database 254 and one verified item data record from the private food items database 256. In such embodiment, an icon, symbol, notation, or other marker may be used to indicate the source of the data record (i.e., whether from a government entity, commercial institution, private individual, etc.).

While the foregoing embodiments (i.e., with multiple verified items for a particular food) present the user with a choice, in another embodiment the user may elect to only review verified items or records in a filtered list (not shown). Still further, the number of data records displayed to the user for review may be significantly reduced.

As noted previously, the item data records in the private food items database 256 are in one embodiment based on manual user input and therefore may include inaccuracies and/or incomplete nutritional information as opposed to the item data records in the public food items database 254. Specifically, item data records in the private food items database 256 are not reviewed or subject to regulation. On the other hand, item data records in the public food items database 254 are, in one embodiment, provided by organizations that have vetted or validated the data and/or are subject to regulation with regard to the content of the nutritional data.

Accordingly, in one embodiment, all item data records in the public food items database 254 are automatically identified as "verified" items and include markers indicating their status as "verified" food items when displayed. In another embodiment, at least some of the item data records in the private food items database 256 may also be identified as "verified" items, but only after such item data records are verified as containing trusted nutrition data. Exemplary methods that may be used by the health tracking system 100 to evaluate item data records in a database (e.g., the private food items database 256) and identify certain ones thereof as "verified" are discussed below.

Method of Determining Verified Item Data Records

Figure 5:
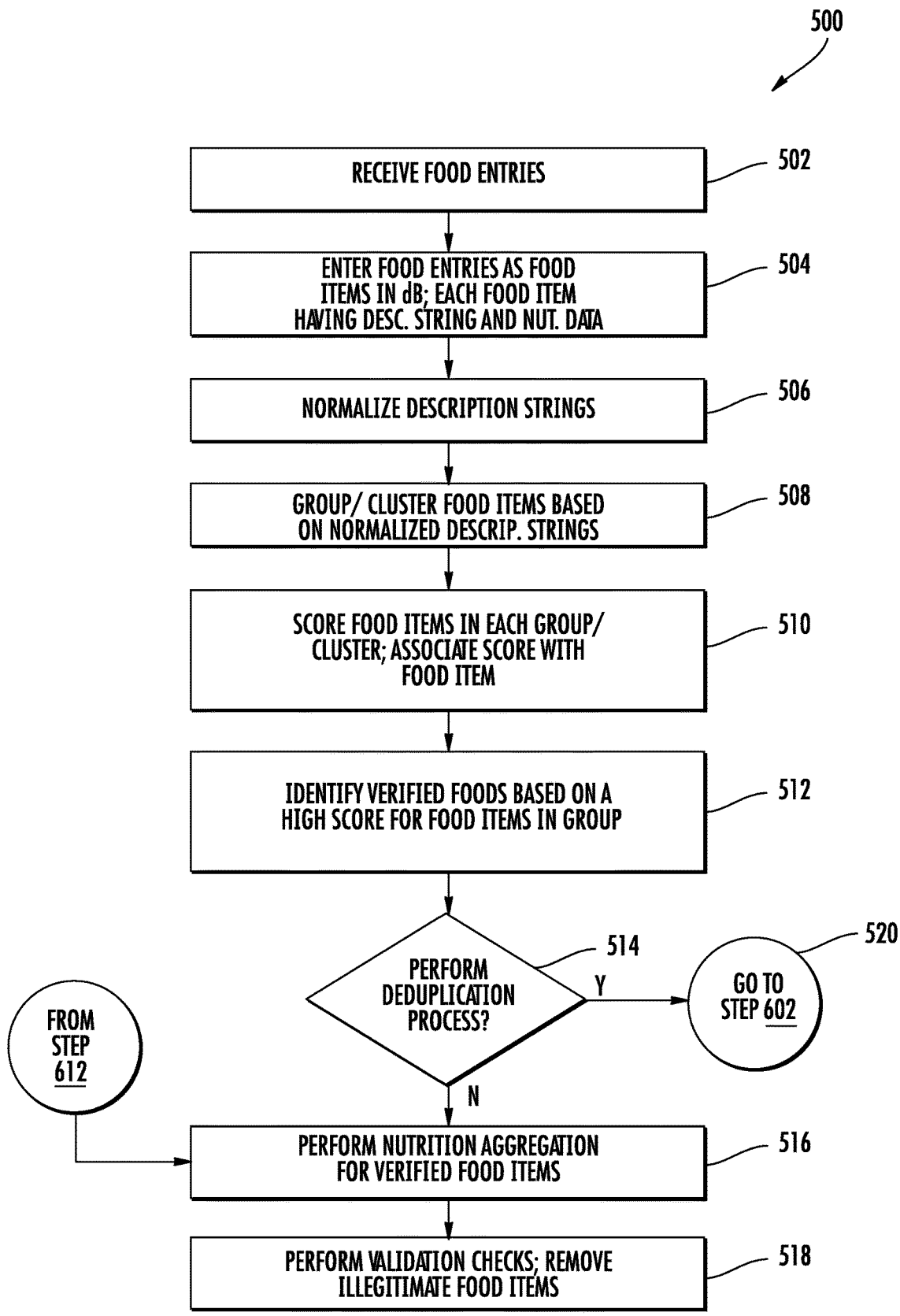
FIG. 5 is a logical flow diagram of a method for identifying verified item data records of the health tracking system of FIG. 1.

With reference now to FIG. 5, a logical flow diagram of an exemplary method 500 of determining verified item data records from the private food items database 256 is disclosed. At step 502 of the method 500, the host server 230 receives data entries from a plurality of health tracking devices 110 controlled by users of the health tracking system 100. In submitting a data entry, the user provides a name of the consumable as a description string and at least some nutrition data relating thereto. In step 504, the crowd sourced food entries are entered as item data records in the private food items database 256, each data record including at least a description string and some nutrition data.

Steps 502 and 504 of the logical flow diagram of FIG. 5 represent data collection relating to consumables by the host server 230 of the health tracking the system 100. As noted previously, the process of crowd sourcing the generation of food records in the private food items database 256 results in numerous duplicate entries for a single food type. Item data records representing the same food item may be represented in multiple free text forms. For example, various users may have entered each of the following description strings for the McDonald's® McChicken sandwich: "McDonalds McChicken," "McChicken," "McDonalds McChicken Sandwich," and "McDonalds McChiken Sandwich." In a further variant, each of these multiple item data records for the same food presents incomplete nutrition data and/or the data between the multiple records is inconsistent. For example, the first record entitled "McDonalds McChicken" may include nutrition data indicating a total of 600 calories, 15 g of total fat content, and no carbohydrate information; the next record entitled "McChicken" may include nutrition data indicating a total of 700 calories, no fat content information, and 25 g of carbohydrates. Various other differences and inconsistencies exist between the other item data records in this example. Accordingly, after a predetermined threshold number of records are collected in the private food items database 256, the health tracking system 100 proceeds to process the item data records in order to identify verified or reliable ones thereof. The steps conducted in this verification process are described below with reference to steps 506 through 518 of FIG. 5.

In step 506, the processing circuitry 232 of the host server 230 normalizes the description strings for each item data record in the private food items database 256. Any of various processes may be used to perform the normalization of the description strings, as will be recognized by those of ordinary skill in the art. For example, the normalization process may involve any of various canonicalization procedures such as removal of hyphens and periods, stemming and lemmatization, case-folding, and so forth.

In step 508, the data records are grouped together into clusters based on the normalized description strings. The grouping results in item data records with identical or similar description strings being mapped to the same group. The grouping of the food item records may be performed using any of various cluster analysis algorithms, such as connectivity based clustering, centroid-based clustering, distribution based clustering, density-based clustering, or any other appropriate clustering algorithm. Any of various computing frameworks may be utilized to perform the clustering algorithm, such as the "GroupByKey( )" function in the Spark open source cluster computing framework.

Figure 7:
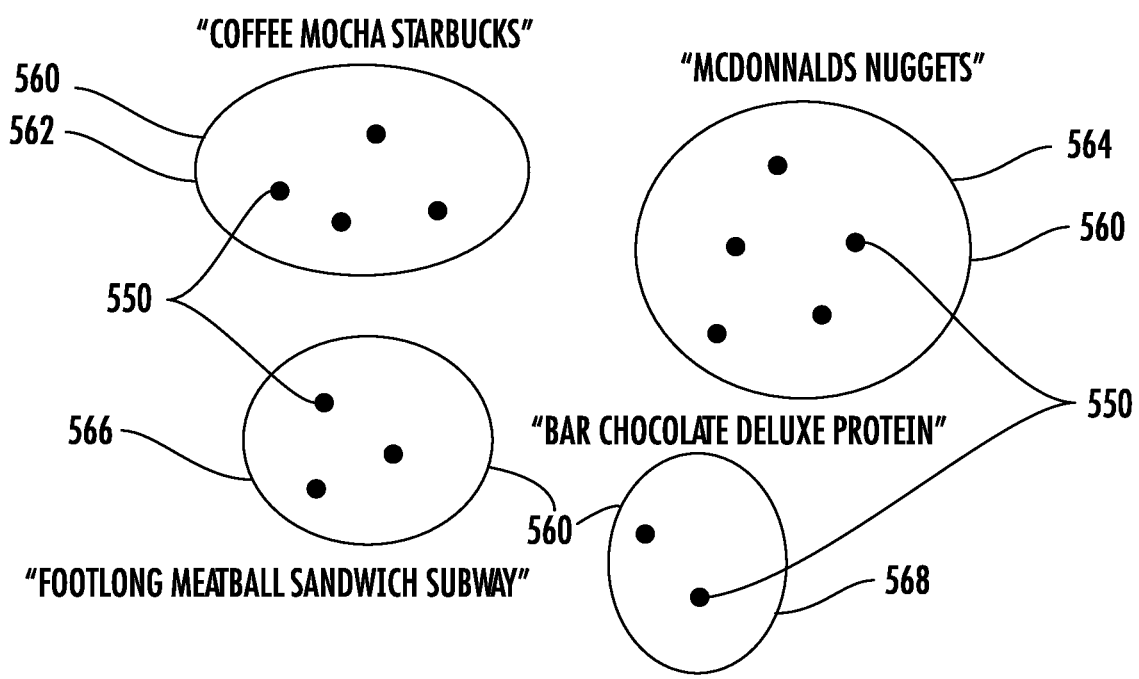
FIG. 7 is an illustration of an exemplary set of food groups resulting from the clustering process of the logical flow diagram of FIG. 5.

FIG. 7 shows an illustration of exemplary item data records grouped together into clusters of the same food group following the clustering process of step 508. In the example of FIG. 7, a plurality of item data records 550 are represented by dots. Each item data record 550 is associated with one of four food groups 560, each the food groups 560 represented by a circle with a plurality of dots encompassed by the circle. The four food groups 560 in the embodiment of FIG. 7 include the "coffee mocha starbucks" group 562, the "mcdonnalds nuggets" group 564, the "footlong meatball sandwich subway" group 566, and the "bar chocolate deluxe protein" group 568. The description string provided for each food group (i.e., the name or title associated with each food group) may be determined based on the most common normalized description string for the item data records 550 in the food group 560. For example, the "mcdonnalds nuggets" food group 564 may include a number of item data records 550 with the same description string as the food group. However, the clustering algorithm also places item data records with related description strings in the same food group. For example, the "mcdonnalds nuggets" food group 564 may include some item data records with the "mcdonnalds nuggets chicken" description string, or the "chicken nuggets mcdonnalds" description string, to name a few.

Figure 8:
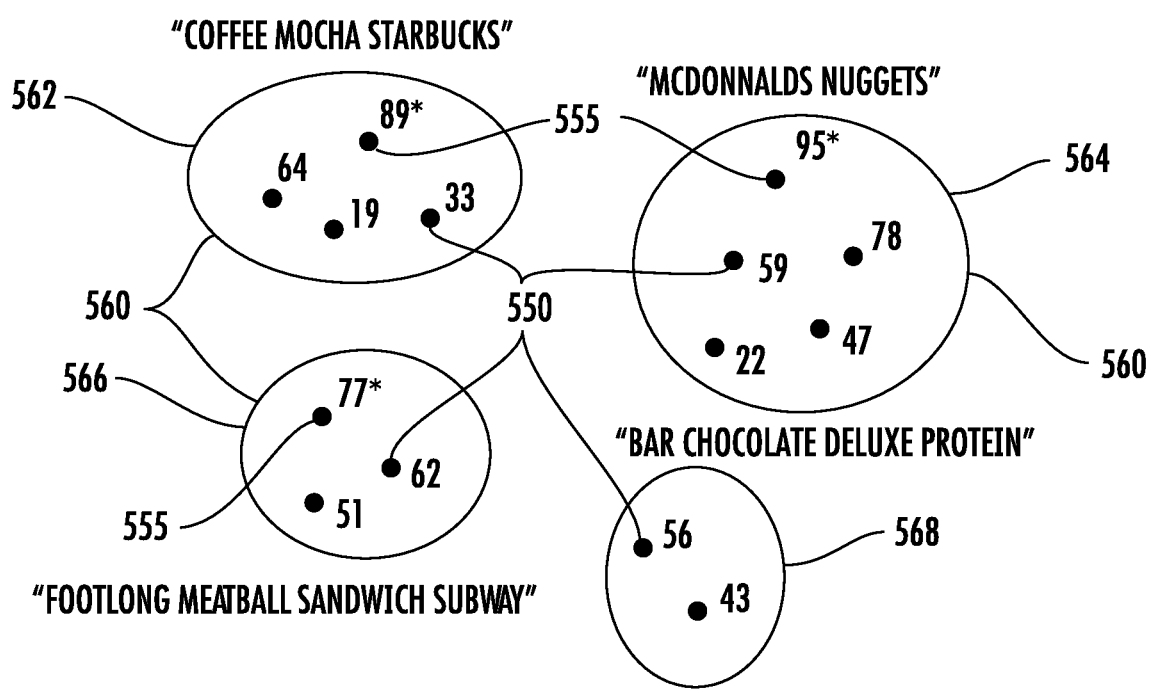
FIG. 8 is an illustration of the exemplary set of food groups with of FIG. 7 with verified item data records identified within each food group.

With reference again to FIG. 5, following the grouping process of step 508, the processing continues to step 510. At step 510, the item data records 550 in each group 560 are individually scored, and each item data record 550 is then associated to its determined score. In other words, during the scoring process, an individual score is determined for each data record in each group, and the determined score is then associated with each data record. FIG. 8 shows an illustration of the food groups 560 with an exemplary score associated with a data record shown next to each food item 550.

The scoring process used to score each item data record may be based on any number of factors. The factors used in the scoring process are intended to identify the record 550 in the food group 560 that contains the most trusted data of all of the records in the food group 560. Exemplary scoring factors may include the number of times the record has been selected by a user to be logged for consumption, the number of different users that have selected the record to be logged, the similarity of the nutrition data contained in the record to that of other records in the group, whether the food item is a public or private food item, as well as any number of additional scoring factors incorporated into the health tracking system 100. All of the foregoing factors are used in a scoring algorithm to arrive at an overall score for the data record. Some factors may be weighed more heavily than others in the scoring algorithm in one embodiment. For example, the number of different users that have logged a particular food item data record may be more heavily weighted than the number of times the food item data record has been logged.

After the scoring algorithm is applied to each item data record 550 in the food group 560, each item data record 550 is associated to its score. As noted in step 512 of FIG. 5, the data record with the highest score in the food group 560 is then identified as the verified item 555 for the food group 560. The private food items database 256 is updated to indicate that the item data record 550 is a verified item 555. In the example of FIG. 8, the verified or reliable item 555 in each food group 560 is identified with an asterisk next to the score associated therewith. For example, the "coffee mocha starbucks" food group 562 of FIG. 8 includes four food item records with the following scores: 89, 64, 19 and 33. An asterisk is shown next to the verified or trustworthy record 555 with the highest score in the group 560 (i.e., the food item with the score of 89).

While FIG. 8 shows exemplary scores for food items with scores between 0 and 100, it will be recognized that any number of different score ranges and different types of scores are possible depending on the scoring algorithm used. For example, accordingly to one scoring algorithm, food items may be ranked by letters (e.g., between "A" and "F"). According to another scoring algorithm, scores may fall in a range between 1,000 and 100,000. Accordingly, it will be recognized that the exemplary scores provided herein are merely for illustration, and any number of different scoring arrangements are possible.

Item data records that are determined to be "verified" in the private food items database 256 are identified as such when a listing of item data records is presented to the user on his or her health tracking device 110. For example, as discussed previously in association with FIG. 4, the verified item may be identified via an associated icon, symbol, notation or other marker to indicate that the item data record has been identified as being "verified". When logging consumption of food items, many users will choose to select only verified items from the list. This not only saves the user time by limiting the number of item data records to review prior to logging a food, but also improves the accuracy of nutrition data entered into the health tracking system for the user.

With reference again to FIG. 8, in at least one embodiment, a verified item is not identified for those food groups 560 having an insufficient number of records. For example, if a food group 560 includes only one or two data records, no verified item data record may be identified for the food group. In FIG. 8, the "bar chocolate deluxe protein" food group 568 only includes two data records, so no verified item is identified for the food group 568.

In another embodiment, multiple verified item data records may be identified for a those food groups having a number of records exceeding a threshold number. In such embodiments, the verified data records are each associated with a high score within the food group, but not necessarily a highest score. For example, if a food group 560 includes one hundred or more records, two verified records may be identified for the food group, a first data record having a score of 97 and a second data record having a score of 95. In this case, the second data record does not have the highest score for the group, but does have a high score within the group, and the second data record is identified as being verified because of its relatively high score within the relatively large food group.

Returning again to FIG. 5, after verified data records within various food groups are identified in step 512, the process continues at step 514, and a determination is made whether to run a deduplication process. The deduplication process is designed to refine the verification process by removing duplicate food groups 560, duplicate data records, and any associated duplicate verified data records. Duplicate food groups and duplicate item data records often result from typographical errors in the identification or description string for item data records. While the clustering process of step 508 properly clusters many of the item data records together in the same food group, the clustering process may not always properly cluster similar item data records 550 into the same food group 560. In particular, the clustering process may not cluster food items with significant misspellings into the same food groups. This may result in duplicate food groups with each of the duplicate food group containing data records for the same food. For example, the clustering process of FIG. 7 has created a "mcdonnalds nuggets" food group ("mcdonnalds" being an improper spelling), but may have also created a "mcdonalds nuggets" food group ("mcdonalds" having a proper spelling). Moreover, because of the particular misspelling associated with the item descriptors, many of the created food groups 560 will include only a limited number of item data records (e.g., one or two food records); and in at least some embodiments, no verified data record may be identified for these food groups with a small number of food items.

Accordingly, in order to properly group item data records in the same group, and to improve the process of identifying verified item data records, the health tracking system 100 may also include a deduplication process. Because the deduplication process may not be performed each time the food items are clustered and verified foods are identified (such as in steps 508 through 512), the deduplication process is shown as an optional step i.e., step 514. If the duplication process is to be performed at step 514, the method of FIG. 5 moves to step 520, and the deduplication process begins. The deduplication process is explained in further detail below with reference to FIG. 6 and the method of steps 602 through 612. Whether the deduplication process is performed at step 514 depends on a number of factors, including the time since the deduplication process was last performed, as explained in further detail below under the heading "Deduplication Process".

With continued reference now to FIG. 5, when it is determined that the deduplication process is not to be performed at step 514, the method continues with step 516, wherein nutrition aggregation is performed for the verified food items. Nutrition aggregation, in one embodiment, involves entering nutrition data for the verified item data record 555 based on other members in the same food group 560. The nutrition data entered into the verified item data record may comprise completion of a missing field of nutrition data and/or an amendment to existing field of nutrition data for the verified item data record. The nutrition data entered into the verified item data record may be determined using any of various mechanisms, including e.g., copying nutrition data from another item data record in the food group, or aggregating nutrition data from one or more other items in the group and entering an average of the nutrition data (such as a mean, mode, median, etc.) for all of the other data records in the food group, or any of various other mechanism. It is noted that data aggregation into the verified data record is optionally performed and in one embodiment may be omitted in favor of retaining the data as entered in the existing verified data record.

Figure 9:
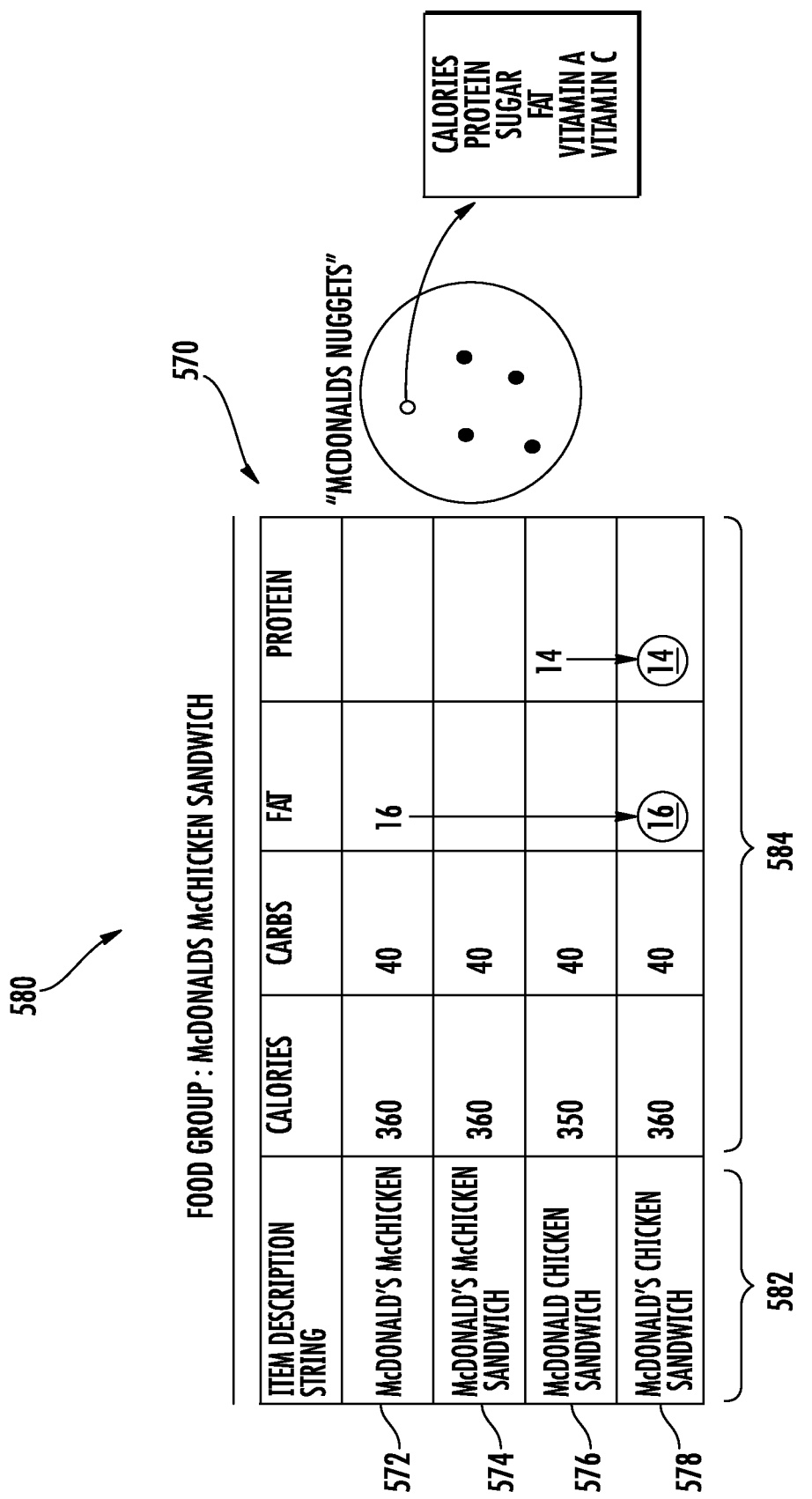
FIG. 9 is a table of item data records illustrating an exemplary nutrition aggregation process of the logical flow diagram of FIG. 5.

FIG. 9 illustrates an exemplary nutrition aggregation process for a food group 570 entitled "mcdonalds mcchicken sandwich". Four item data records 572, 574, 576 and 578 are included in the food group 570. FIG. 9 shows the nutritional data contained in each of the four item data records 572, 574, 576, and 578 in a table 580 along with the associated description strings 582. Assume for the sake of example, that of the four items, the item 578 having the description string "McDonald's Chicken Sandwich" received the highest score and is therefore identified as the verified item data record. However, as shown in the example, item 578, the verified item, is missing certain nutrition data; specifically, the data record does not include the fat and protein data. Per the nutrition aggregation process, the incomplete nutrition data is completed, in this embodiment, by copying fat and protein data from other members of the food group. In particular, the fat content of "16 g" has been copied from the first item 572 and inserted in the nutrition data for the verified or reliable item 578 to complete the missing fat content. Similarly, the protein data of "14 g" has been copied from the third item 576 and inserted into the nutrition data for the verified item 578 to complete the missing protein content.

While FIG. 9 illustrates copying of nutrition data from other item data records in the food group, it will be recognized that the entry of new nutrition data for the verified food item 578 may be determined using different mechanisms. For example, if the fat content for food item 574 was listed as "14 g", the system may take the average fat content of food item 572 (i.e., "16 g") and food item 574 (i.e., "14 g") to determine a fat content of "15 g" which is entered in the nutrition data for the verified item data record 578. Additionally, in another embodiment, only select item data records from the food group 570 may be used to complete the nutrition content data for the verified item 578. For example, the health tracking system 100 may only use (such as for averaging or copying as discussed above) nutrition data from the item data records having the top ten highest scores from the food group when it is determined that the nutrition data for a verified item must be completed.

Figure 10:
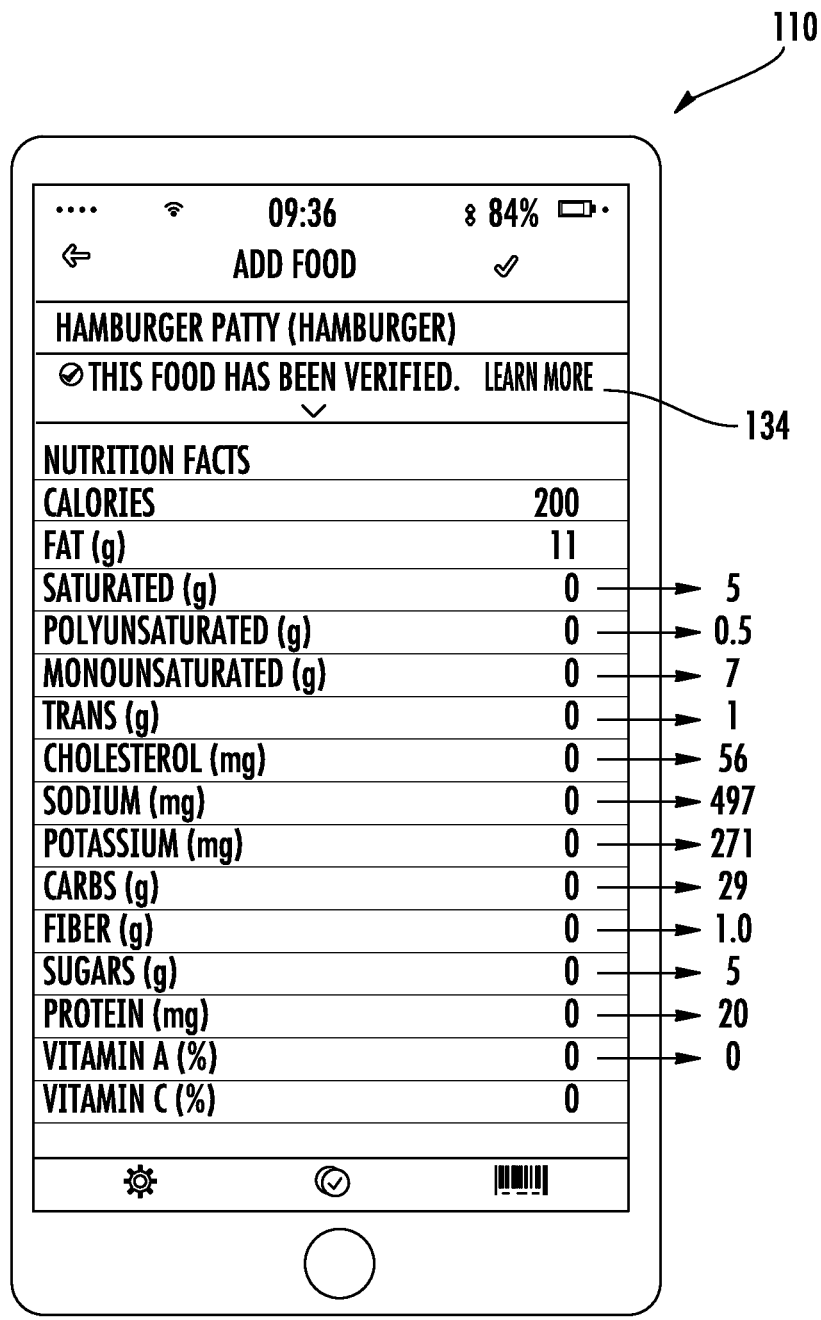
FIG. 10 is a plan view of a graphical user interface of the display device prior to the nutrition aggregation process of the logical flow diagram of FIG. 5.

FIG. 10 shows an exemplary verified food item data record presented to a user on a display screen of a health tracking device 110. The numbers on the display screen to the left of the arrows show the nutrition data for the verified food item data record prior to the nutrition aggregation step 516. The numbers to the right of the arrows show the nutrition data for the verified food item data record following the nutrition aggregation step. As shown in FIG. 10, while the nutrition data is complete with respect to calories and fat content prior to the nutrition aggregation step, the remaining nutrition data is incomplete for that record. However, pursuant to the nutrition aggregation step, the numbers to the right of the arrow are entered for the verified food item data record based on the nutrition data from other records in the same food group as the verified food item data record.

In at least one embodiment, the nutrition aggregation step results in an amended verified item data record in the private foods database 256, with the amended verified item data record having different nutrition data after the nutrition aggregation step than before the nutrition aggregation step (i.e., more complete data and/or different data which represents an average across many records). The amended verified data record is stored in replacement to the pre-aggregation record. However, in another embodiment, the nutrition aggregation step may result in the automatic creation of a new item data record in the private foods database; this newly created record comprises the verified or trustworthy item data record. This new item data record in the private foods database is identical to the identified item for the food group (determined via the methods discussed above for identification of a verified item), but further includes the additional and/or amended nutrition data following the nutrition aggregation step (i.e., more complete data and/or different data which represents an average across many records). In this embodiment, the new item data record in the private foods database becomes the verified data record for the food group, and the previously identified verified data record is demoted from being a verified food item.

With continued reference to FIG. 5, after verified item data records are identified and the nutrition data for the verified records is improved with the nutrition aggregation step 516 (optionally), the method continues with step 518 and one or more validation checks are performed. The validation checks provide a set of validation rules that a verified item data records must follow. If any of the validation rules is violated, the validation check process demotes the verified item data record to a non-verified item data record. Examples of validation rules that may be performed on the verified item data records are provided in the paragraphs below.

A first validation rule for verified item data records is that all nutrient values must be non-negative. For example, if a particular item described as "breastfeeding" is promoted to a verified item data record, but the calorie count is negative 500 calories, it is clear that this item is problematic, and should not be a verified item. In this case, the verified item data record is demoted to a non-verified item data record.

Another validation rule for verified item data records is that all of nutrition data cannot be zero or null, i.e., non-zero values must be entered in at least one nutrition data field. In other words, at least some nutrition data must be entered for each verified data record. For example, if the item data record having the descriptor of "nothing" is promoted to a verified item, but all nutrition data is zero or null, it is clear that this item is problematic, and should not be a verified item. As another example, if the verified item data record having the descriptor of "bean burrito" has no nutrition data at all, i.e., all nutrition data is zero or null, the item data record will be demoted to a non-verified item data record. In at least one embodiment, there may be an exception to this validation rule for data records having a description string that indicates the item is water, unsweetened tea, or other consumable recognized as having nutritional values of zero.

Yet another validation rule for verified item data records is that the nutrition data must meet a predetermined relation between calories and macro-nutrients. For example, the system may pre-define a relationship between calories and the aggregate sum of carbohydrates, protein and fat. In one example, the total calories may be required to almost equal a weighted sum of carbohydrates, protein and fat, within a 10% error margin. If the relationship is not met within the error margin (e.g., +/−10%), the data record may be demoted from a verified or reliable item data record. As another example, the system may further pre-define a relationship between fats. In this example, the total fat for a food item must be greater than or equal to the sum of trans fat, saturated fat, poly-saturated fat, and monounsaturated fat. In yet another example, the system may pre-define relationship between total carbohydrates and certain other nutrients. Specifically, the total carbohydrates must be greater than or equal to the sum of fiber and sugar in one example.

Still another validation rule for verified items may include that data records in certain food categories must have certain specific nutrition data. For example, food items categorized as "dairy," "eggs," or "cheese" must have some value other than zero for one or more of: fat, saturated fat, sodium, potassium, protein, vitamin A, calcium and iron. As another example, food items categorized as "meat," "poultry," "fish," "dry beans," "eggs," or "nuts" must have some value other than zero for one or more of: fat, sodium, potassium, protein, calcium and iron. As yet another example, food items categorized as "fruits" or "vegetables" must have some value other than zero for one or more of: sodium, potassium, carbohydrates, fiber, sugar, vitamin A and vitamin C. If any of the item data records in these categories fail to meet the verification rule, the item data record is demoted to a non-verified item data record.

While a number of examples of validation rules are provided above, it will be recognized that numerous additional validation rules are possible. The system 100 may incorporate one or more of these validation rules, as well as any additional validation rules, into the validation process.

Deduplication Process

As noted previously, in step 514 of FIG. 5, a deduplication process may be performed after verified or reliable item data records are identified. The deduplication process 600 is intended to detect duplicates in the verified item data records, which may result in one example from typographical errors in the identification string. The deduplication process reduces or completely eliminates the number of duplicate verified item data records for any given food item type in the private foods database 256. In other words, the system 100 is configured to eliminate duplicates of verified item data records for the same consumable item, as only one record should be the verified data record for any particular food.

The deduplication process may be performed based on any number of preexisting conditions. For example, in at least one embodiment the deduplication process may be performed periodically (e.g., once a week) or one time for each time the method 500 for identifying verified or trustworthy item data records is performed. As noted previously, the deduplication process occurs only after the description strings for each item data record have been normalized (in step 506 of FIG. 5), the records have been grouped into clusters (in step 508) with each cluster having an identification string, the item data records within each cluster have been scored (in step 510), and at least one verified item has been identified within each cluster (in step 512). However, the clustering process of step 508 may result in a large number of groups (e.g., over one million clusters), wherein each group contains only a limited number of item data records (e.g., one or two records in each cluster). It is likely that many of the groups containing only a limited number of data records should have been clustered together with items in other groups (i.e., the clustering process did not properly cluster some data records into the same group). Thus, in an attempt to better identify verified item data records, the system 100 may perform a deduplication process (in step 514 of FIG. 5) after one or more verified item data records have been identified (in step 512). A logical flow diagram for one exemplary embodiment of the deduplication process is shown in FIG. 6.

Figure 6:
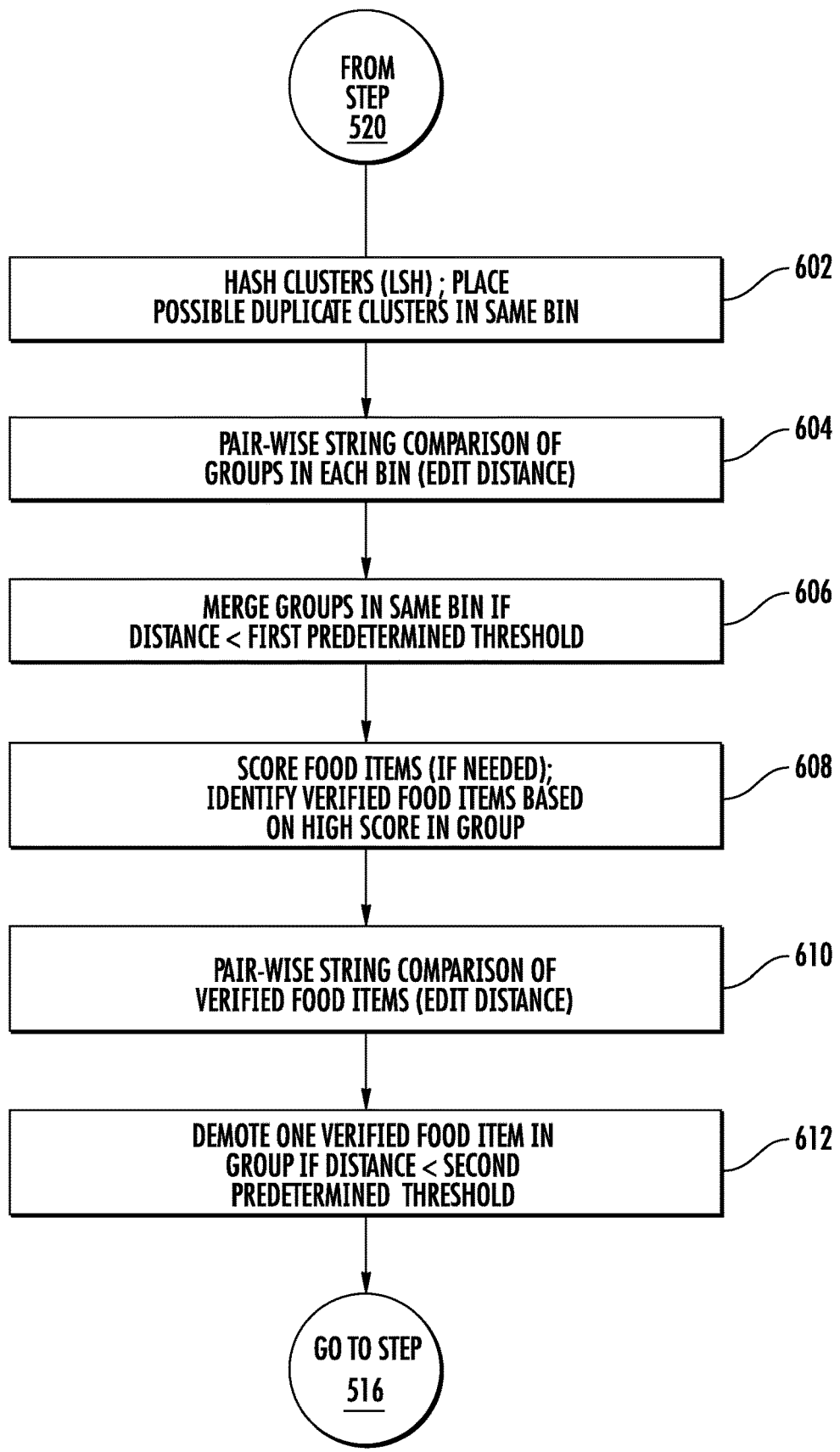
FIG. 6 is a logical flow diagram of a method for the deduplication of the verified item data records identified in the logical flow diagram of FIG. 5.

As shown in FIG. 6, the deduplication process begin with step 602, where each of the groups is hashed. In at least one embodiment, the hashing is performed using a local sensitivity hashing (LSH) algorithm. In order to prepare the groups for the LSH algorithm, the identification string associated with each group is converted into a sparse vector using three-character shingles, and each single is mapped to its index order alphabetically (e.g., "aaa"→0, "aab"→1. etc.). The LSH algorithm reviews the groups resulting from the clustering process of step 508 of FIG. 5 and hashes into a single bin the groups which are candidates of being duplicates based on the similarities of the description strings for the groups. In other words the LSH algorithm identifies those groups (i.e., clusters of item data records from step 508) having item data records that are likely to identify the same food, and places those groups in a common bin for further processing. It will be recognized by those of ordinary skill in the art that LSH involves a number of parameters including (1) m (the number of bins to hash data into), (2) numRows (the number of times to hash a vector such that numRows separate hash functions are generated), (3) the number of times to chop numRows (such that each band will have numRows/numBand hash signatures) and, (4) miniClusterSize (a post processing filter function that excludes clusters below a threshold). The use of different variables selected for each of the foregoing parameters, will result in the LSH algorithm preparing different numbers of bins with different groups placed in the various bins.

Figure 11:
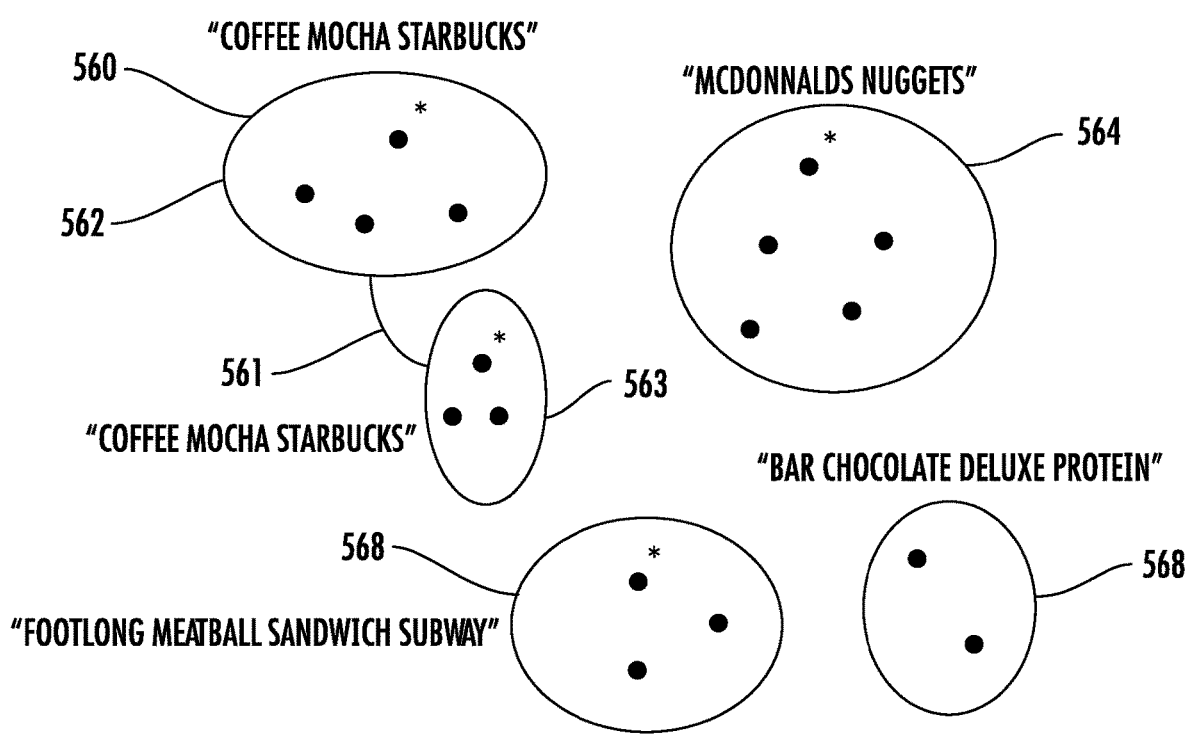
FIG. 11 is an illustration of the exemplary set of food groups with two of the food groups placed in a bin during the deduplication process of FIG. 6.

FIG. 11 shows an illustration of an identified bin resulting from the LSH algorithm. FIG. 11 is similar to FIG. 7, and includes the same four groups 562, 564, 566 and 568 identified during the clustering process of step 508, plus an additional group 563 also identified during the clustering process of step 508. The additional group 563 is entitled "coffee mocha starbucks" (note the distinction between the words "coffee" and "coffee" in groups 562 and 563). The LSH process of step 602 has placed the "coffee mocha starbucks" group 562 in the same bin as the "coffee mocha starbucks" group 563 (a common bin noted in FIG. 11 by connecting line 561 indicating that the two groups 562 and 563 are now coupled together in the same bin). The use of bins simplifies the subsequent pair-wise comparison of the deduplication process (i.e., step 604 described below) because only those groups in the same bin are compared to each other rather than a pair-wise comparison over all groups identified from the clustering step 508. While FIG. 11 shows only two groups in the same bin (i.e., groups 562 and 563), it will be recognized that some bins resulting from the LSH process of step 602 may contain more than two groups in a single bin.

Returning now to FIG. 6, following the LSH processing in step 602, the deduplication process 600 has identified various bins containing different groups (i.e., different clusters) that should potentially be considered the same group. The deduplication process 600 continues at step 604 with a pair-wise comparison of the groups in each bin. For example, in the illustration of FIG. 11, a pair-wise string comparison of the "coffee mocha starbucks" group 562 is made with the "coffee mocha starbucks" group 563. A pair-wise comparison of other groups in the same bin is then also made (i.e., a pair-wise comparison of all groups in a single bin is performed). Groups in other bins can also be compared at the same time (i.e., in parallel) by the processing circuitry 232 of the host server 230 since each bin is independent of the other bins.

The pair-wise comparison of groups in bins may be performed using any number of algorithms. For example, in at least one embodiment, a pair-wise comparison of the description strings is performed using an Edit Distance operation. The Edit Distance operation is used as similarity measure, and the distance returned from the Edit Distance operation is normalized by dividing by the larger of the two description string lengths. Then, if the distance between the two description strings is sufficiently small, the pair is assumed as being duplicates.

Figure 12:
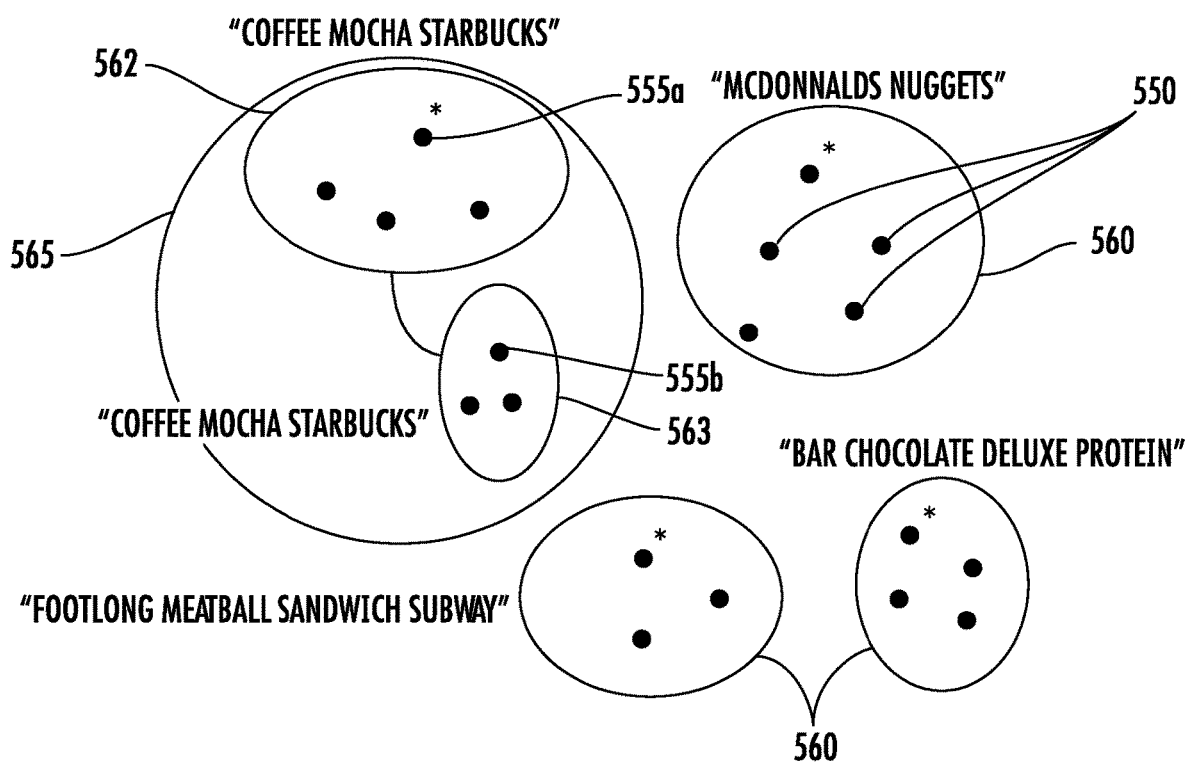
FIG. 12 is an illustration of the exemplary set of food groups of FIG. 11 with the two food groups placed in the bin merged into a single food group.

Following the string comparison of the groups in step 604, the groups having a distance less than the predetermined threshold are merged into the same group in step 606. For example, as shown in FIG. 12, the distance between the "coffee mocha starbucks" group 562 and the "coffee mocha starbucks" group 563 is determined using the Edit Distance operation. After this, the distance returned from the Edit Distance operation is normalized to [0,1], by dividing by the larger of the two string lengths. Because the distance returned from the Edit Distance operation is less than a predetermined threshold distance (e.g., 0.3), the two groups 562 and 563 are assumed to be duplicates and merged into a new "coffee mocha starbucks" group 565. The new "coffee mocha starbucks" group 565 is a combined group including all of the items 550 from the original "coffee mocha starbucks" group 562 and all of the item records from the original "coffee mocha starbucks" group 563.

Following step 606 any new group resulting from two or more merged groups may include more than one verified item data record. For example, in the illustration of FIG. 12, the new "coffee mocha starbucks" group 565 may contain one verified item from the original "coffee mocha starbucks" group 562 (i.e., verified item 555a), and one verified item from the original "coffee mocha starbucks" group 563 (i.e., verified item 555b). Accordingly, in step 608 the same process as previously discussed previously in association with steps 510 and 512 of FIG. 5 is performed wherein all items in a group are scored (if not previously scored) and a high score for at least one item in the group is identified. The item data record (or item records) associated with this high score is then identified as the verified item data record for the new group (e.g., see verified item data record 555a for the new "coffee mocha starbucks" group 565 in FIG. 12). Previously verified items that fail to meet the high score standard for the new group are then demoted and are no longer regarded as verified items (e.g., see previous verified item 555b in the new "coffee mocha starbucks" group 565 in FIG. 12).

It should be noted that following step 608 of FIG. 6, the deduplication process may have identified even more verified items than existed prior to the start of the deduplication process 600. The reason for this is that numerous small groups containing only a small number of item data records (e.g., one or two item data records) will have been merged with other groups (whether large or small). As a result, some groups that were previously too small to identify a verified item for the group will become sufficiently large to identify a verified item. For example, if two groups each containing two item data records are merged together into a new group containing four item records, this new group may now contain a sufficient number of item data records to identify a verified data record for the group. Accordingly, while none of the four item data records in this new group was an identified as a verified item prior to the start of the deduplication process 600, at least one of these four item data records will be an identified verified item following the deduplication process.

After the process identifies the new verified or trustworthy item data records for each of the groups in step 608, duplicates may still exist amongst the identified verified item data records. For example, because of the probabilistic nature of LSH, there may still be duplicate verified item data records that are the result of misspellings of the item records. Therefore, in order to detect these duplicate verified item data records that still remain in the private food items database 256, the deduplication process continues with step 610.

In step 610, another pair-wise string comparison is performed, with this pair-wise string comparison only between the records that have been identified as verified item data records. In at least one embodiment, the pair-wise string comparison of verified item data records is performed by first grouping the verified item data records together by the first letter of any brand name (if a brand name exists in the description string). By grouping the verified items in this manner, the pair-wise comparison process may be performed in a parallel manner. Any of various methods may be used to compare the description strings of the verified items. For example, a distance between each verified item may be determined using the Edit Distance operation on the description strings.

Following the pair-wise string comparison operation (e.g., the Edit Distance operation) of step 610, a distance between two verified items is determined. In step 612, this distance is compared to a predetermined threshold distance in order to determine if one of the two verified or reliable item data records should be demoted. The predetermined threshold distance for determining verified item duplicates in step 612 is typically less than the predetermined threshold distance in step 606 for determining group duplicates. For example, while the threshold distance associated with step 606 may be 0.3, the threshold distance associated with step 612 may be 0.1. Accordingly, it will be recognized that a stricter standard is associated with the pair-wise comparison of verified item data records than with the previous pair-wise comparison of groups.

The verified item data record that is demoted to a non-verified item data record in step 612 is typically the verified item having the lower score of the two verified items. For example, if the pairwise comparison of a first verified item having a score of 97 and a second verified item having a score of 95 is made, and the distance between the two verified item data records is less than the predetermined threshold returned from the Edit Distance operation (e.g., less than 0.1), the second verified item will be demoted to a non-verified item and the first verified item will remain a verified item because the second verified item has a lower score than the first verified item. Accordingly, it will be recognized that although the deduplication of groups in steps 604 and 606 may actually increase the number of verified items during the deduplication process 600 (as noted above), the deduplication of verified items in steps 610 and 612 results in a reduced number of verified item data records during the deduplication process 600.

The foregoing method may be accomplished with the assistance of a computer program, such as the activity or health tracking program 248 described above, stored in the memory 234 and executed by the processor 232 of the host server 230. The above described system and method solves a technological problem common in industry practice related to effective and efficient presentation of health data, and particularly food and nutrition to a user. Moreover, the above-described system and method improves the functioning of the computer/device by allowing health data to be effectively communicated to the user along with a graphical user interface that makes food item recommendations by presenting verified or reliable food item data records to the user.

Portions of the system and methods described herein may be implemented using one or more programs or suitable software code, such as the health tracking app on the health tracking device 110 and the health tracking program 248 on the host server 230, both described above, each of which may reside within the memory of the respective computing devices as software or firmware. Such programs and code may be stored in the memory and executed by the processor of the display device or a system server or other computer in communication with the display device. A computer program product implementing an embodiment disclosed herein may therefore comprise one or more computer-readable storage media storing computer instructions translatable by processing circuitry/logic, a CPU, or other data processing device to provide an embodiment of a system or perform an embodiment of a method disclosed herein. Computer instructions may be provided by lines of code in any of various languages as will be recognized by those of ordinary skill in the art.

A "computer-readable medium" may be any type of data storage medium that can store computer instructions and/or data, including, read-only memory (ROM), random access memory (RAM), hard disks (HD), data cartridges, data backup magnetic tapes, floppy diskettes, flash memory, optical data storage, CD-ROMs, or the like. The computer readable medium can be, by way of example, only but not by limitation, an electronic, magnetic, optical, electromagnetic, infrared, or semiconductor system, apparatus, system, device, or computer memory. The computer readable medium may include multiple computer readable media storing computer executable instructions, such as in a distributed system or instructions stored across an array. A "non-transient computer-readable medium" may be any type of data storage medium that can store computer instructions, including, but not limited to the memory devices discussed above.

The above described system and method solves a technological problem common in industry practice related to effective and efficient presentation of health data to a user for analysis and consideration by the user. Moreover, the above-described system and method improves the functioning of the computer device by causing food and nutrition data to be easily presented to a user in a health tracking system, while also allowing the user to manipulate the food and nutrition data or otherwise make use of the nutrition data in the manner that he or she sees fit. In the foregoing description, various operations may be described as multiple discrete actions or operations in turn, in a manner that may be helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

The foregoing detailed description of one or more exemplary embodiments of the health tracking system with verification of food item data records has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed exemplary embodiments and other features and functions, or alternatives thereof, may be desirably combined into many other different embodiments, systems or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the exemplary embodiments contained herein.

What is claimed is:

1. A method of operating a health tracking system, comprising:
    aggregating a plurality of crowd-sourced data records from a plurality of health tracking devices, each crowd-sourced data record of the plurality of crowd-sourced data records comprising a user generated description string relating to one of a plurality of consumables from a plurality of health tracking devices;
    clustering the plurality of crowd-sourced data records into a plurality of clusters, wherein the clustering is based on a similarity of the user generated description string such that each data record in a cluster has a similar user generated descriptive string;
    scoring each of the plurality of crowd-sourced data records in each of the plurality of clusters;
    after said scoring, determining one or more reliable crowd-sourced data records in each of the plurality of clusters based on the scoring of each of the crowd-sourced data records and a number of crowd-sourced data records in each of the plurality of clusters;
    identifying at least one first data record and at least one second data record in one of the plurality of clusters that have duplicate name entries and inconsistent nutrition entries, wherein the identified at least one first data record is one of the reliable crowd-sourced data records;
    merging a first nutrition information from the at least one first data record with a second nutrition information from the at least one second data record to create a merged reliable data record;
    after said scoring and merging, performing a validation check on said merged reliable data record, wherein said validation check includes determining that the said first nutrition information and said second nutrition information meet a predetermined relationship between calories and macronutrients;
    storing the plurality of crowd-sourced data records in a crowd-sourced database; and
    responsive to receiving a search query for a consumable, returning the merged reliable data record corresponding to the consumable;
    wherein more than one reliable crowd-sourced data record is identified for one of the plurality of clusters in response to the number of crowd-sourced data records in said one of the plurality of clusters being greater than a threshold number.

2. The method of claim 1, further comprising:
    removing one or more of the plurality of clusters having typographical errors.

3. The method of claim 1, where the merging comprises averaging the first nutrition information and the second nutrition information to create the merged reliable data record.

4. The method of claim 3, where the merging comprises averaging the first nutrition information, the second nutrition information, and a third nutrition information of the merged reliable data record to create the merged data record.

5. The method of claim 1, further comprising: normalizing the user generated description string of each of the plurality of crowd-sourced data records into a canonicalized form, wherein the clustering is based on the normalized user generated description string.

6. The method of claim 1, wherein one of the determined one or more reliable crowd-sourced data records is demoted and no longer determined to be reliable based on the merging.

7. The method of claim 1, wherein the scoring of a record of the plurality of crowd-sourced data records is based on a first number of times the record is selected as logged for consumption by a user, a second number of users that have selected the record as logged for consumption, and a similarity of the record to other records in an assigned cluster of the plurality of clusters of the record and the other records.

8. The method of claim 1 wherein after said scoring, said aggregating nutrition information in the plurality of crowd-sourced data records from the plurality of health tracking devices results in a plurality of merged reliable data records in said one of the plurality of clusters.

9. A health tracking system, comprising:
a network interface;
a crowd-sourced database;
a processor; and
a non-transient computer readable medium comprising a plurality of instructions which are configured to, when executed by the processor, cause the health tracking system to:
receive a plurality of crowd-sourced data records relating to a plurality of consumables from a plurality of health tracking devices;
cluster the plurality of crowd-sourced data records into a plurality of clusters based on a similarity of descriptive strings such that each data record in a cluster has a similar descriptive string;
scoring each of the plurality of crowd-sourced data records in each of the plurality of clusters;
identifying at least one reliable data record for each of the plurality of clusters, said identification of at least one reliable data record based on said scoring and a number of data records in each of the plurality of clusters;
after said scoring, aggregate nutrition information in the plurality of crowd-sourced data records from the plurality of health tracking devices to create a plurality of merged reliable data records, each of said merged reliable data records including an aggregation of nutrition information from two or more of said plurality of crowd-sourced data records within one of the plurality of clusters, and one of said two or more of said plurality of crowd-sourced data records being the reliable merged data record for said one of the plurality of clusters;
perform validation checks on each of said merged reliable data records, wherein each of said validation checks includes determining whether the aggregate nutrition information for said merged reliable data record meets a predetermined relationship between calories and macronutrients;
when it is determined that the aggregate nutrition information for said merged reliable data record meets the predetermined relationship between calories and macronutrients, identifying said merged reliable data record as a verified data record of a plurality of verified data records;
when it is determined that the aggregate nutrition information for said merged reliable data record does not meet the predetermined relationship between calories and macronutrients, omitting to identify said merged reliable data record as one of the plurality of verified data records; and
responsive to a search query for a consumable by a first health tracking device, return at least one verified data record of the plurality of verified data records to the first health tracking device, the returned verified data record received from a different health tracking device of the plurality of health tracking devices that sent any portion of a crowd-sourced data record associated with the consumable;
wherein more than one reliable data record is identified for one of the plurality of clusters in response to the number of crowd-sourced data records in said one of the plurality of clusters being greater than a threshold number.

10. The health tracking system of claim 9, wherein the calories for said merged reliable data record is a calorie value, and wherein the macronutrients for said merged reliable data record includes a carbohydrate value, a protein value, and a fat value, and wherein the health tracking system further comprises instructions which are configured to, when executed by the processor, cause the health tracking system to:
identify at least one first data record that is duplicative of at least one second data record based on the nutrition information;
merge the at least one first data record with the at least one second data record to create one of the plurality of merged reliable data records;
identify a first caloric value associated with the carbohydrate value, a second caloric value associated with the protein value, and a third caloric value associated with the fat value; and
calculate an aggregate macronutrient caloric value based on the first caloric value, the second caloric value, and the third caloric value; and
wherein the predetermined relationship between calories and macronutrients is a predetermined threshold between the calorie value for the merged reliable data record and the aggregate macronutrient caloric value.

11. The health tracking system of claim 10, where the at least one first data record comprises a user generated typographic error.

12. The health tracking system of claim 10, where the at least one first data record comprises a user generated nutrition error.

13. The health tracking system of claim 9, where the nutrition information in the plurality of crowd-sourced data records is aggregated on a periodic basis.

14. The health tracking system of claim 9, where the health tracking system further comprises instructions which are configured to, when executed by the processor, cause the health tracking system to:
update the at least one verified data record based on subsequent user generated input.

15. The health tracking system of claim 9, where the at least one verified data record is associated with a reliability score based on said scoring.

16. The health tracking system of claim 9 wherein after said scoring, said aggregating nutrition information in the plurality of data records results in a plurality of merged reliable data records in said one of the plurality of clusters.

* * * * *